(12) United States Patent
Bremer et al.

(10) Patent No.: US 6,808,762 B2
(45) Date of Patent: Oct. 26, 2004

(54) OXABICYCLOOCTANES

(75) Inventors: Matthias Bremer, Darmstadt (DE);
Michael Heckmeier, Bensheim (DE);
Melanie Klasen-Memmer,
Heuchelheim (DE); Harald Lannert,
Fränkisch-Crumbach (DE)

(73) Assignee: Merck Patent GmbH, Darmstadt (DE)

( * ) Notice: Subject to any disclaimer, the term of this patent is extended or adjusted under 35 U.S.C. 154(b) by 86 days.

(21) Appl. No.: 10/260,530

(22) Filed: Oct. 1, 2002

(65) Prior Publication Data
US 2003/0215580 A1 Nov. 20, 2003

(30) Foreign Application Priority Data
Oct. 1, 2001 (DE) .......................................... 101 48 485

(51) Int. Cl.[7] .................. C09K 19/32; C09K 19/34;
C09K 19/30; C07D 311/96; C07D 319/06
(52) U.S. Cl. .............. 428/1.1; 252/299.61; 252/299.62;
252/299.63; 549/356; 549/369; 549/398;
549/399
(58) Field of Search ................................ 549/369, 356,
549/398, 399; 428/1.1; 252/299.61, 299.62, 299.63

(56) References Cited
FOREIGN PATENT DOCUMENTS
JP      10237075      *   9/1998

OTHER PUBLICATIONS
English translation of JP 10–237075 by computer, http://www4.ipdl.jpo.go.jp/Tokujitu/PAJdetail.ipdl?N0000=60&N0120=01&N2001=2&N3001=H10–237075.*

* cited by examiner

*Primary Examiner*—Shean C. Wu
(74) *Attorney, Agent, or Firm*—Millen, White, Zelano & Branigan, P.C.

(57) ABSTRACT

The present invention relates to oxabicyclooctanes of the general formula I.

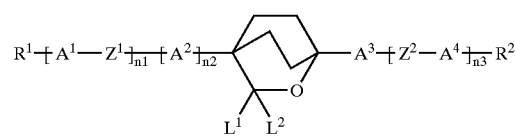

in which
$R^1$, $R^2$, $A^1$, $A^2$, $A^3$, $A^4$, $L^1$, $L^2$, n1, n2 and n3 have the meanings specified in claim 1, and to their use in liquid-crystalline media.

19 Claims, No Drawings

OXABICYCLOOCTANES

The present invention relates to oxabicyclooctanes of formula I, to the use thereof in liquid-crystalline media and to liquid-crystal and electro-optical display elements containing the liquid-crystalline media according to the invention.

Liquid crystals are used, in particular, as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP cells (deformation of aligned phases), guest/host cells, TN structure having a twisted nematic structure, STN cells (supertwisted nematic), SBE cells (superbirefringence effect) and OMI cells (optical mode interference). The most common display devices are based on the Schadt-Helfrich effect and have a twisted nematic structure.

The liquid-crystal materials must have good chemical and thermal stability and good stability to electric fields and electromagnetic radiation. Furthermore, the liquid-crystal materials should have relatively low viscosity and give short response times, low threshold voltages and high contrast in the cells.

Furthermore, they should have a suitable mesophase, for example a nematic or cholesteric mesophase for the above-mentioned cells, at conventional operating temperatures, i.e. in the broadest possible range above and below room temperature. Since liquid crystals are generally used in the form of mixtures of a plurality of components, it is important that the components are readily miscible with one another. Further properties, such as the electrical conductivity, the dielectric anisotropy and the optical anisotropy, must satisfy different requirements depending on the cell type and area of application. For example, materials for cells having a twisted nematic structure should have positive dielectric anisotropy and low electrical conductivity.

For example, media of large positive dielectric anisotropy, broad nematic phases, relatively low birefringence, very high resistivity, good UV and temperature stability and low vapor pressure are desired for matrix liquid-crystal displays having integrated non-linear elements for switching individual pixels (MLC displays).

Matrix liquid-crystal displays of this type are known. Examples of non-linear elements which can be used for individual switching of individual pixels are active elements (i.e. transistors). This is then referred to as an "active matrix", and a differentiation can be made between two types:

1. MOS (metal oxide semiconductor) or other diodes on silicon wafers as substrates.
2. Thin-film transistors (TFTs) on a glass plate as substrate.

Use of single-crystal silicon as the substrate material limits the display size, since even modular assembly of the various part-displays results in problems at the joints.

In the case of the more promising type 2, which is preferred, the electro-optical effect used is usually the TN effect. A differentiation is made between two technologies: TFTs comprising compound semiconductors, such as, for example, CdSe, or TFTs based on polycrystalline or amorphous silicon. Intensive work is being carried out worldwide on the latter technology.

The TFT matrix is applied to the inside of one glass plate of the display, whilst the other glass plate carries the transparent counterelectrode on the inside. Compared with the size of the pixel electrode, the TFT is very small and has virtually no adverse effect on the image. This technology can also be extended to fully color-compatible image displays, where a mosaic of red, green and blue filters is arranged in such a way that each filter element is located opposite a switchable pixel.

The TFT displays usually operate as TN cells with crossed polarizers in transmission and are illuminated from the back.

The term MLC displays here covers any matrix display containing integrated non-linear elements, i.e., in addition to the active matrix, also displays comprising passive elements, such as varistors or diodes (MIM=metal-insulator-metal).

MLC displays of this type are particularly suitable for TV applications (for example pocket TV sets) or for high-information displays for computer applications (laptops) and in automobile or aircraft construction. In addition to problems with respect to the angle dependence of the contrast and the response times, problems arise in MLC displays owing to inadequate resistivity of the liquid-crystal mixture [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210–288 Matrix LCD Controlled by Double Stage Diode Rings, p.141 ff, Paris; STROMER, M., Proc. Eurodisplay 84, September 1984: Design of Thin Film Transistors for Matrix Adressing of Television Liquid Crystal Displays, p.145 ff, Paris]. With decreasing resistance, the contrast of an MLC display drops, and the problem of after-image elimination can occur. Since the resistivity of the liquid-crystal mixture generally drops over the life of an MLC display owing to interaction with the internal surfaces of the display, a high (initial) resistance is very important in order to obtain acceptable service lives. In particular in the case of low-voltage mixtures, it was hitherto not possible to achieve very high resistivities. It is furthermore important that the resistivity increases as little as possible with increasing temperature and after heating and/or exposure to UV radiation. Also particularly disadvantageous are the low-temperature properties of the prior art mixtures. It is required that crystallization and/or smectic phases do not occur even at low temperatures, and that the temperature dependence of the viscosity is as low as possible. MLC displays of the prior art thus do not satisfy current requirements.

Besides liquid-crystal displays which use backlighting, i.e. are operated transmissively and optionally transflectivity, there is also interest in reflecting liquid-crystal displays. These reflected liquid-crystal displays use the ambient light for information display. They thus consume significantly less energy than backlit liquid-crystal displays of corresponding size and resolution. As the TN effect is distinguished by very good contrast, such reflective displays can be read even under bright ambient conditions. This is known even about simple, reflective TN displays like those in, for example, wristwatches and pocket calculators. The principle can also be applied, however, to sophisticated, higher-resolution active-matrix-activated displays such as TFT displays for example. Here, as is the case in the generally used transmissive TFT-TN displays, the use of liquid crystals of low birefringence ($\Delta n$) is necessary in order to achieve low optical retardation (d·$\Delta n$). This low optical retardation results in a generally acceptable low angle-of-view dependence of the contrast (cf. DE 30 22 818). In reflective displays, the use of liquid crystals having low birefringence is even more important than in transmissive displays, since in reflective displays the effective layer thickness traversed by the light is approximately twice that of transmissive displays having the same layer thickness.

Advantages of reflective displays compared with transmissive displays include, in addition to the lower power consumption (no backlighting necessary), the greater economy in terms of space, resulting in very small overall depth, and the lessening of the problems caused by temperature gradients owing to differential heating by the backlighting.

There thus continues to be a great demand for MLC displays having very high resistivity at the same time as a broad operating temperature range, short response times even at low temperatures, and low threshold voltage which do not have these disadvantages or only do so to a reduced extent.

In the case of TN (Schadt-Helfrich) cells, media are desired which facilitate the following advantages in the cells:

broadened nematic phase range (in particular down to low temperatures), switchability at extremely low temperatures (outdoor use, automobile, avionics), increased stability on exposure to UV radiation (longer life), low threshold (drive) voltage low birefringence for improved observation angle range.

The media available from the prior art do not enable these advantages to be achieved while simultaneously retaining the other parameters.

In the case of supertwisted cells (STN), media are desired which enable greater multiplexibility and/or lower threshold voltages and/or broader nematic phase ranges (particularly at low temperatures). To this end, a further broadening of the parameter latitude available (clearing point, smectic-nematic transition or melting point, viscosity, dielectric quantities, elastic quantities) is urgently desired.

None of the previously known series of compounds having a liquid-crystalline mesophase include a single compound which meets all these requirements. Consequently, as a rule, mixtures of from 2 to 35, preferably from 3 to 18, compounds are prepared in order to obtain substances which can be used as liquid-crystalline phases.

It is an object of the invention to provide MLC displays which do not have the abovementioned disadvantages or have them only to a lesser extent, preferably at the same time having very high resistivities and low threshold voltages. In addition, the compounds according to the invention which have a negative dielectric anisotropy are also suitable for VA applications. Upon further study of the specification and appended claims, further objects and advantages of this invention will become apparent to those skilled in the art.

The substances used hitherto for this purpose always had certain drawbacks, for example inadequate stability with respect to exposure to heat, light or electric fields, disadvantageous mesophases, elastic and/or dielectric properties.

It has now been found that these and other objects can be achieved if compounds and media according to the invention are used in liquid-crystal displays.

In particular, it was found that the oxabicyclooctanes according to the invention are eminently suitable as components of liquid-crystal media. With their aid, stable liquid-crystalline media can be obtained which are particularly suitable for liquid-crystalline displays, such as those described above. The novel compounds are especially distinguished by high thermal stability, which is advantageous for a high "holding ratio", and have advantageous clearing point and birefringence values. The compounds according to the invention are suitable, in particular, for TFT, OCB, VA and IPS applications.

By providing the oxabicyclooctanes according to the invention, the range of liquid-crystalline substances suitable from various application points of views for preparing liquid-crystalline mixtures is quite generally broadened considerably.

The oxabicyclooctanes according to the invention are colorless in the pure state and form liquid-crystalline mesophases in a temperature range favorably situated for electro-optical use. They are chemically-, thermally- and light-stable.

The invention therefore includes oxabicyclooctanes of the general formula I

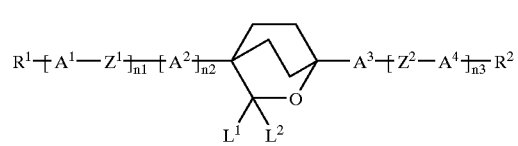

in which $L^1$ and $L^2$ independently of one another, are H or F, $R^1$ and $R^2$ independently of one another, are CN or halogen or alkyl having from 1 to 12 C atoms which is unsubstituted or mono- to perhalo-substituted by halogen, CN or $CF_3$, it also being possible for one or more $CH_2$ groups to be replaced, in each case independently of one another, by —O—, —S—, —CO—, —CO—O—, —O—CO—, —O—CO—O—, -◇-, (i.e., 1,3-cyclobutylene), —CH=CH—, —CH=CF—, —CF=CF— or —C≡C— in such a way that S and/or O atoms are not linked directly to one another, $A^{1-4}$ are, independently of one another: trans-1,4-cyclohexylene, in which one or two nonadjacent $CH_2$ groups can be replaced by —O— and/or —S—; 1,4-phenylene, in which one or two CH groups can also be replaced by N; 1,4-cyclohexenylene; 1,4-bicyclo-(2,2,2)-octylene; piperidine-1,4-diyl-; naphthalene-2,6-diyl; decahydro-naphthalene-2,6-diyl; or 1,2,3,4-tetrahydronaphthalene-2,6-diyl; where the above rings can be monosubstituted or polysubstituted by F, Cl, CN, $CF_3$, $Z^1$ and $Z^2$ each, independently of one another, are —$CH_2O$—, —$OCH_2$—, —$CF_2O$—, —$OCF_2$—, —COO—, —OCO—, —$CF_2CF_2$—, —$CH_2CH_2$—, —$(CH_2)_4$—, —$(CH_2)_3O$—, —$O(CH_2)_3$—, —$CF_2CH_2$—, —CH=CH—, —CH=CF—, —CF=CF—, —C≡C— or a single bond, n1 is 0 or 1, n2 is 0 or 1, and n3 is 0, 1 or 2 with the proviso that n1=0, if n2=0.

The invention also relates to the use of oxabicyclooctanes of formula I as components of liquid-crystalline media.

The invention also relates to a liquid-crystalline medium comprising at least two liquid-crystalline components containing at least one oxabicyclooctane of formula I.

The invention also relates to a liquid-crystal display element, especially an electro-optical display element, which as the dielectric contains a liquid-crystalline medium according to the invention.

If $R^1$ and/or $R^2$ are an alkyl radical and/or an alkoxy radical, this can be straight-chain or branched. It is preferably straight-chain, has 1, 2, 3, 4, 5, 6 or 7 C atoms and therefore preferably means methyl, ethyl, propyl, butyl, pentyl, hexyl, heptyl, ethoxy, propoxy, butoxy, pentoxy, hexoxy or heptoxy, also octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-3-, 4- or 5-oxahexyl, 2-, 3-, 4-, 5- or 6-oxaheptyl, 2-, 3-, 4-, 5 -, 6- or 7-oxaoctyl, 2-, 3-, 4-, 5-, 6-, 7- or 8-oxanonyl, 2-, 3-, 4-, 5-, 6-, 7-, 8- or 9-oxadecyl.

If $R^1$ and/or $R^2$ are an alkyl radical in which a $CH_2$ group has been replaced by —CH=CH—, this can be straight-chain or branched. Preferably it is straight-chain and has from 2 to 10 C atoms. In particular, it is therefore vinyl, prop-1- or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

If $R^1$ and/or $R^2$ are an alkyl radical in which one $CH_2$ group has been replaced by —O— and by —CO—, these are preferably adjacent. They therefore comprise an acyloxy group —CO—O— or an oxycarbonyl group —O—CO—. Preferably these are straight-chain and have 2 to 6 C atoms. In particular, they therefore are acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonyl methyl, ethoxycarbonyl-methyl, propoxycarbonylmethyl, butoxycarbonyl methyl, 2-(methoxycarbonyl)ethyl, 2-(ethyloxycarbonyl)ethyl, 2-(propoxycarbonyl)ethyl, 3-(methoxycarbonyl)propyl, 3-(ethoxycarbonyl)propyl or 4-(methoxy-carbonyl)butyl.

If $R^1$ and/or $R^2$ are an alkyl radical in which one $CH_2$ group has been replaced by unsubstituted or substituted —CH=CH— and an adjacent $CH_2$— group has been replaced by CO or CO—O or O—CO, said alkyl radical can be straight-chain or branched. Preferably it is straight-chain and has from 4 to 13 C atoms. In particular, it therefore is acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If $R^1$ and/or $R^2$ are an alkyl or alkenyl radical monosubstituted by CN or $CF_3$, said radical is preferably straight-chain. The substitution by CN or $CF_3$ can be in any position.

If $R^1$ and/or $R^2$ are an alkyl or alkenyl radical at least monosubstituted by halogen, said radical is preferably straight-chain, and halogen is preferably F or Cl. In the case of polysubstitution, the halogen is preferably F. These resulting radicals also include perfluorinated radicals. In the case of monosubstitution, the fluorine or chlorine substituent can be in any position, but is preferably in the ω position.

If one of the rings $A^{1-4}$ is trans-1,4-cyclohexylene, in which one or two nonadjacent $CH_2$ groups are replaced by O and/or S, the following structures are preferred:

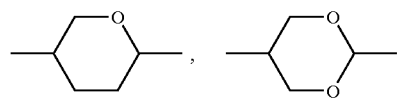

and their mirror images.

If one of the rings $A^{1-4}$ is 1,4-phenylene, in which one or two CH groups are replaced by N, the following structures are preferred:

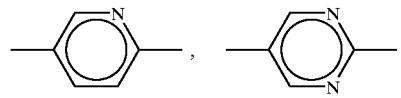

and their mirror images.

If one of the rings $A^{1-4}$ is 1,4 phenylene, which is mono or polysubstituted with F, Cl, CN or $CF_3$, the following structures are preferred:

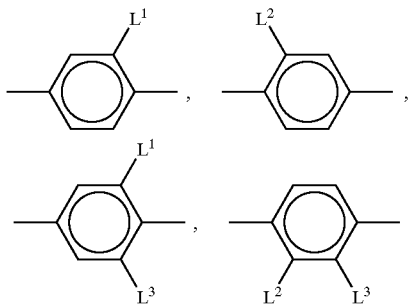

in which $L^{1-3}$, independently of one another, are the said substituents, but preferably F.

The cyclohexenylene-1,4-diyl radical preferably has the following structures:

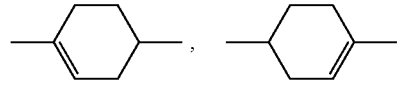

Preferred compounds of the general formula I are those in which n1=0. Particularly preferred compounds of the general formula I are those in which n2=0, too.

Particularly preferred are oxabicyclooctanes of the general formula (Ia),

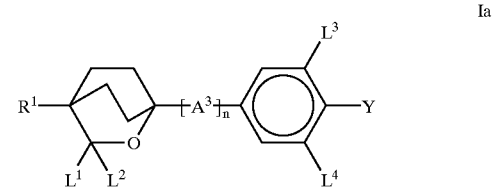

in which $A^3$ is

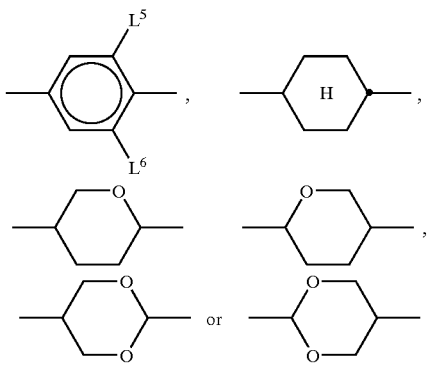

$L^{1-6}$ each, independently of one another, are H or F,

Y is F, Cl, CN or an alkyl or alkoxy radical having from 1 to 6 C atoms which is substituted with one or more halogen atoms, in which radical one or more $CH_2$ groups can also be replaced by —O— or —CH=CH—, O atoms not being linked directly to one another, n is 0 or 1.

Here, Y is preferably F, Cl, CN, $CF_3$, $CF_2H$, $OCF_3$, $OCF_2H$, $OCFHCF_3$, $OCFHCH_2F$, $OCFHCHF_2$, $OCF_2CH_3$, $OCF_2CH_2F$, $OCF_2CHF_2$, $OCF_2CF_2CF_2H$, $OCF_2CF_2CH_2F$, $OCFHCF_2CF_3$, $OCFHCF_2CHF_2$, $OCFHCFHCF_3$, $OCH_2CF_2CF_3$, $OCF_2CF_2CF_3$, $OCF_2CFHCHF_2$, $OCF_2CH_2CHF_2$, $OCFHCF_2CHF_2$, $OCFHCFHCHF_2$, $OCFHCH_2CF_3$, $OCH_2CFHCF_3$, $OCH_2CF_2CHF_2$, $OCF_2CFHCH_3$, $OCF_2CH_2CHF_2$, $OCFHCF_2CH_3$, $OCFHCFHCHF_2$, $OCFHCH_2CF_3$, $OCH_2CF_2CHF_2$, $OCH_2CFHCHF_2$, $OCF_2CH_2CH_3$, $OCFHCFHCH_3$, $OCFHCH_2CHF_2$, $OCH_2CF_2CH_3$, $OCH_2CFHCHF_2$, $OCH_2CH_2CHF_2$, $OCHFCH_2CH_3$, $OCH_2CFHCH_3$, $OCH_2CH_2CHF_2$, $OCClFCF_3$, $OCClFCClF_2$, $OCClFCHF_2$, $OCFHCCl_2F$, $OCClFCHF_2$, $OCClFCClF_2$, $OCF_2CHCl_2$, $OCF_2CHCl_2$, $OCF_2CCl_2F$, $OCF_2CClFH$, $OCF_2CClF_2$, $OCF_2CF_2CClF_2$, $OCF_2CF_2CCl_2F$, $OCClFCF_2CF_3$, $OCClFCF_2CHF_2$, $OCClFCF_2CClF_2$, $OCClFCFHCF_3$, $OCClFCClFCF_3$, $OCCl_2CF_2CF_3$, $OCClHCF_2CF_3$, $OCClFCF_2CF_3$, $OCClFCClFCF_3$, $OCF_2CClFCHF_2$, $OCF_2CF_2CCl_2F$, $OCF_2CCl_2CHF_2$, $OCF_2CH_2CClF_2$, $OCClFCF_2CFH_2$, $OCFHCF_2CCl_2F$, $OCClFCFHCHF_2$, $OCClFCClFCF_2H$, $OCFHCFHCClF_2$, $OCClFCH_2CF_3$, $OCFHCCl_2CF_3$, $OCCl_2CFHCF_3$, $OCH_2CClFCF_3$, $OCCl_2CF_2CF_2H$, $OCH_2CF_2CClF_2$, $OCF_2CClFCH_3$, $OCF_2CFHCCl_2H$, $OCF_2CCl_2CFH_2$, $OCF_2CH_2CCl_2F$, $OCClFCF_2CH_3$, $OCFHCF_2CCl_2H$, $OCClFCClFCHF_2$, $OCFHCFHCCl_2F$, $OCClFCH_2CF_3$, $OCFHCCl_2CF_3$, $OCCl_2CF_2CFH_2$, $OCH_2CF_2CCl_2F$, $OCCl_2CFHCF_2H$, $OCClHCClFCF_2H$, $OCF_2CClHCClH_2$, $OCF_2CH_2CCl_2H$, $OCClFCFHCH_3$, $OCF_2CClFCCl_2H$, $OCClFCH_2CFH_2$, $OCFHCCl_2CFH_2$, $OCCl_2CF_2CH_3$, $OCH_2CF_2CCHlH_2$, $OCCl_2CFHCFH_2$, $OCH_2CClFCFCl_2$, $OCH_2CH_2CF_2H$, $OCClHCClHCF_2H$, $OCH_2CCl_2CF_2H$, $OCClFCH_2CH_3$, $OCFHCH_2CCl_2H$, $OCClHCFHCClH_2$, $OCH_2CFHCCl_2H$, $OCCl_2CH_2CF_2H$, $OCH_2CCl_2CF_2H$, $CH=CF_2$, $OCH=CF_2$, $CF=CF_2$, $OCF=CF_2$, $CF=CHF$, $OCF=CHF$, $CH=CHF$, $OCH=CHF$, in particular F, Cl, CN, $CF_3$, $CHF_2$, $OCF_3$, $OCHF_2$, $OCFHCF_3$, $OCFHCHF_2$, $OCFHCHF_2$, $OCF_2CH_3$, $OCF_2CHF_2$, $OCF_2CHF_2$, $OCF_2CF_2CHF_2$, $OCF_2CF_2CHF_2$, $OCFHCF_2CF_3$, $OCFHCF_2CHF_2$, $OCF_2CF_2CF_3$, $OCF_2CF_2CClF_2$, $OCClFCF_2CF_3$ or $CH=CHF_2$.

Particularly preferably, Y is F, Cl, CN, $OCF_3$ or $OCHF_2$.

The compounds of the formula Ia generally have a high positive dielectric anisotropy Δε and a very high clearing point.

Particularly preferred, in addition, are oxabicyclooctanes of the general formula Ib,

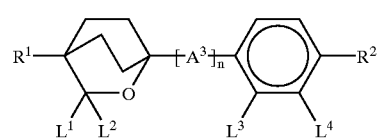

in which $A^3$ is

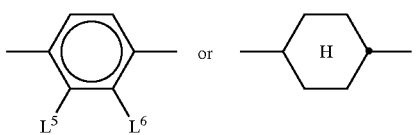

$L^{1-6}$ each, independently of one another, are H or F, $R^1$ and $R^2$ have the meanings specified above, and n is 0 or 1, with the proviso that at least one of the groups $L^3$, $L^4$, $L^5$ and $L^6$ is F.

Here, $R^2$ is preferably straight-chain alkyl or oxaalkyl having from 1 to 8 C atoms or alkenyl or oxaalkenyl having from 2 to 7 C atoms.

The compounds of the general formula Ib generally have a negative dielectric anisotropy Δε, and a low value for the birefringence Δn and a high clearing point.

In the oxabicyclooctanes according to the invention, $L^1$ and $L^2$ preferably have identical meanings, i.e. are either both H or both F.

Particularly preferred oxybicyclooctanes of the general formula Ia are the following compounds:

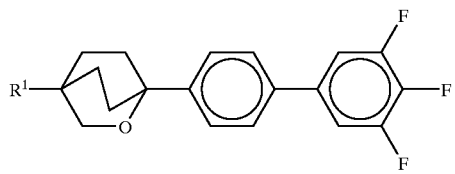

$R^1 = C_3H_7$:

Δε=15.6; Δn=0.147; K 79 N (68.0) I

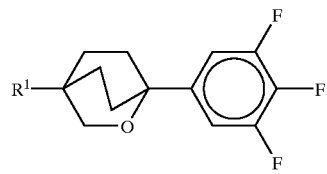

$R^1 = C_3H_7$:

9
Δε=19.6; Δn=0.099; K 161 I
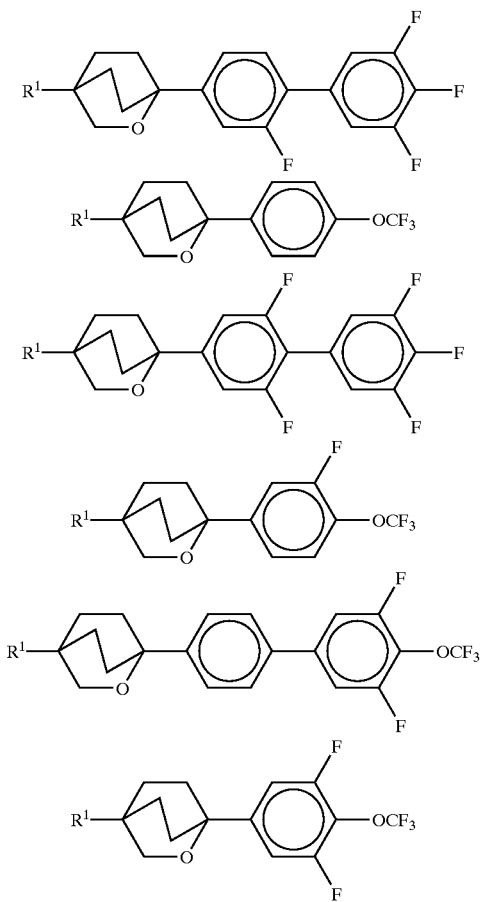
R¹=C₃H₇:
Δε=21.8; Δn=0.099
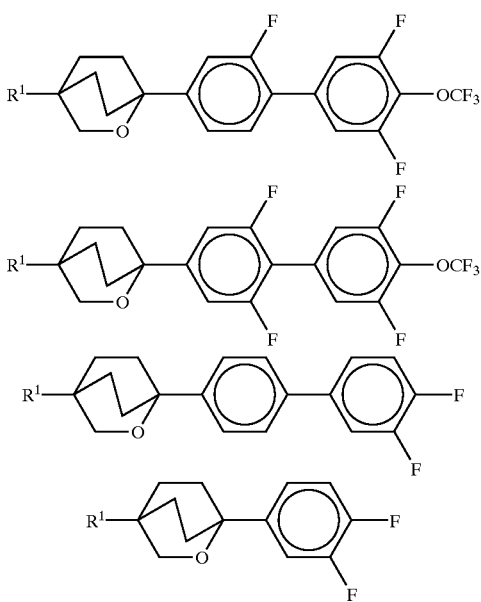
R¹=C₃H₇:
10
Δε=14.7; Δn=0.107
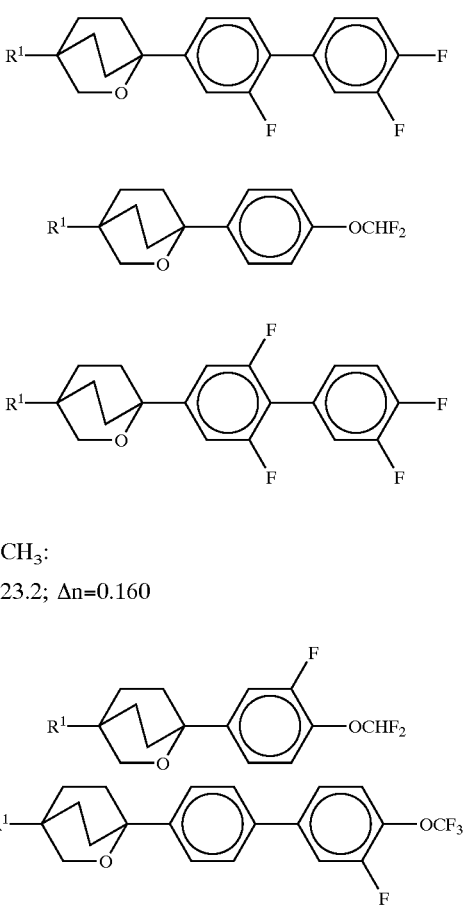
R¹=CH₃:
Δε=23.2; Δn=0.160
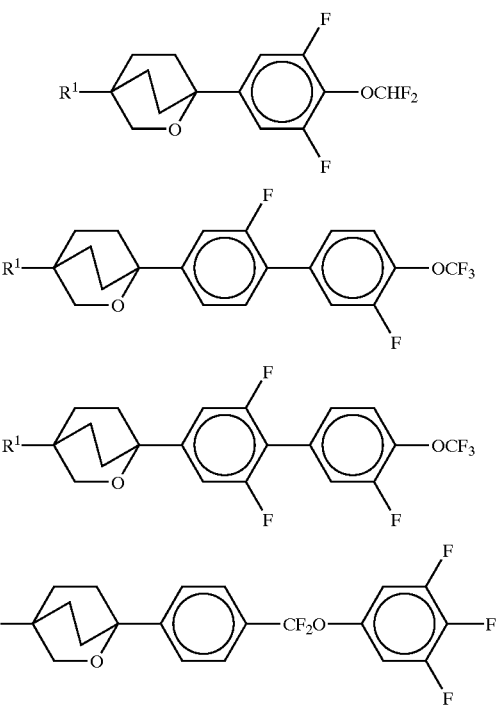
R¹=C₅H₁₁:

Δε=26.9; Δn=0.131
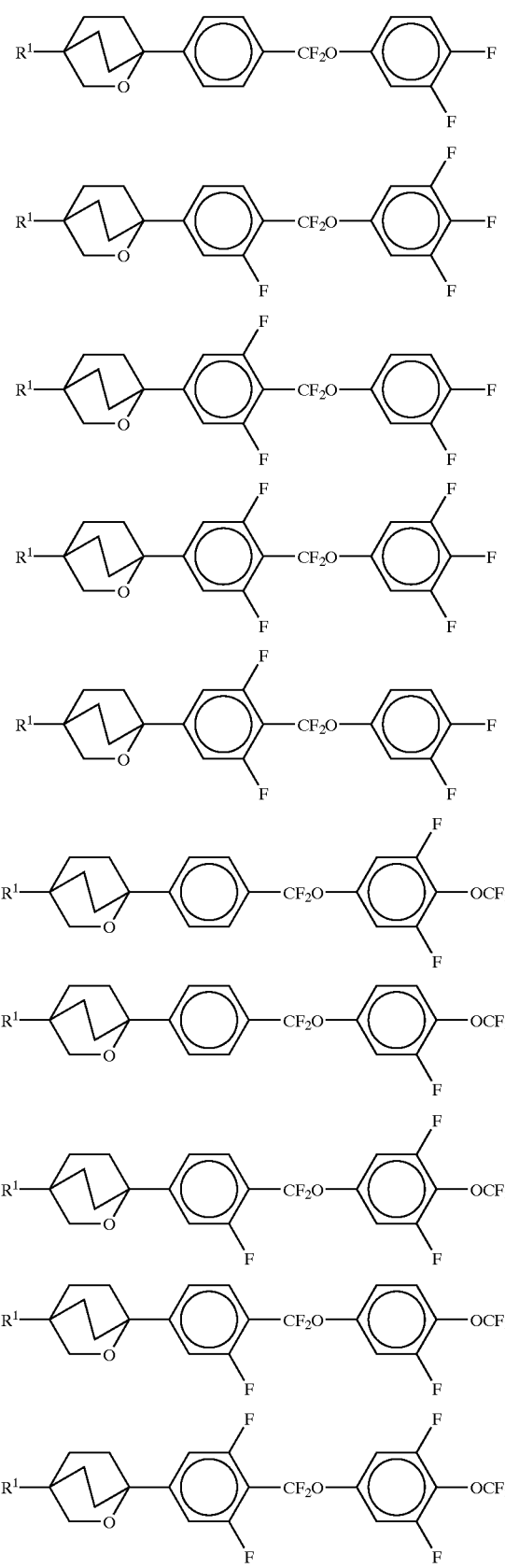
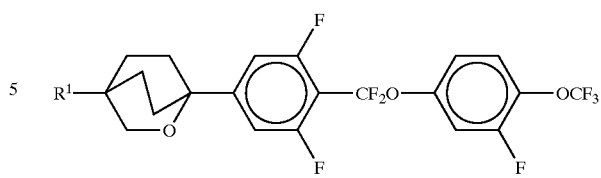
Particularly preferred oxabicyclooctanes of the general formula Ib are the following compounds:
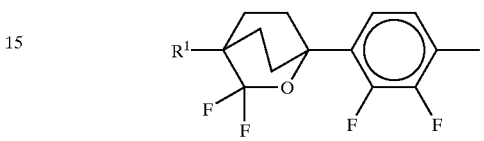
$R^1=C_3H_7$:
Δε=−6.3; Δn=0.090
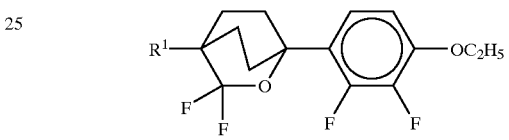
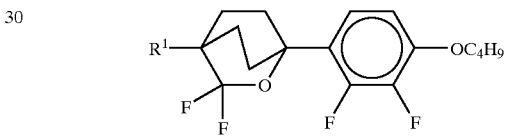
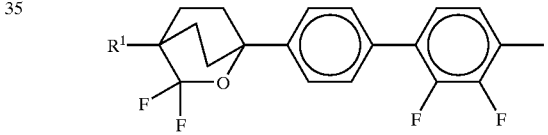
$R^1=C_5H_{11}$:
Δε=−5.4; Δn=0.150
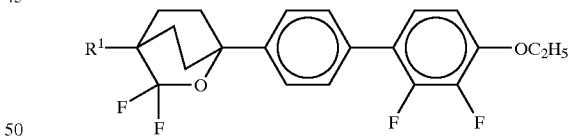
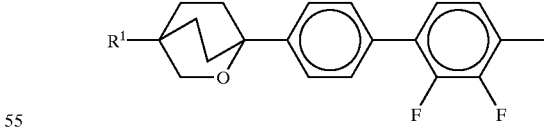
$R^1=C_3H_7$:
Δε=−1.0; Δn=0.140
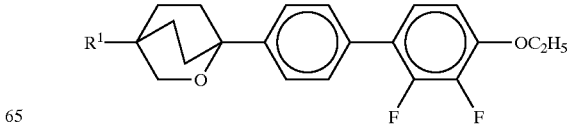

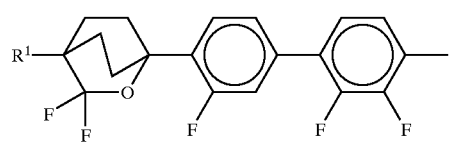
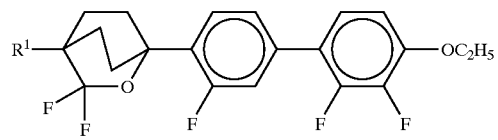
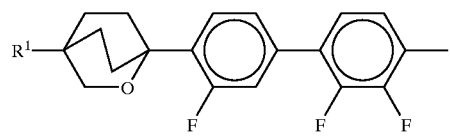
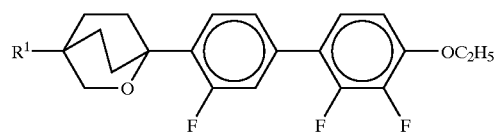
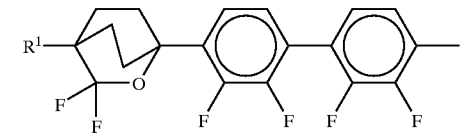
$R^1=C_3H_7$:
$\Delta\epsilon=-6.0; \Delta n=0.143$
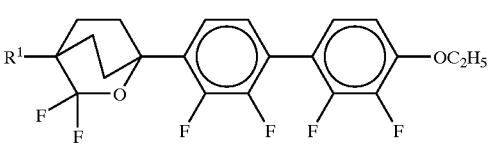
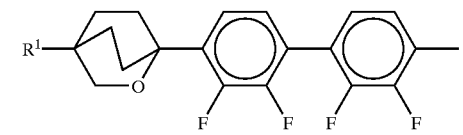
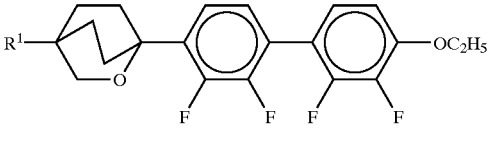
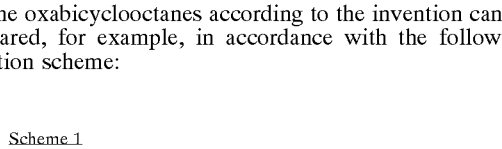
The oxabicyclooctanes according to the invention can be prepared, for example, in accordance with the following reaction scheme:
Scheme 1
($L^1, L^2$: H or F)
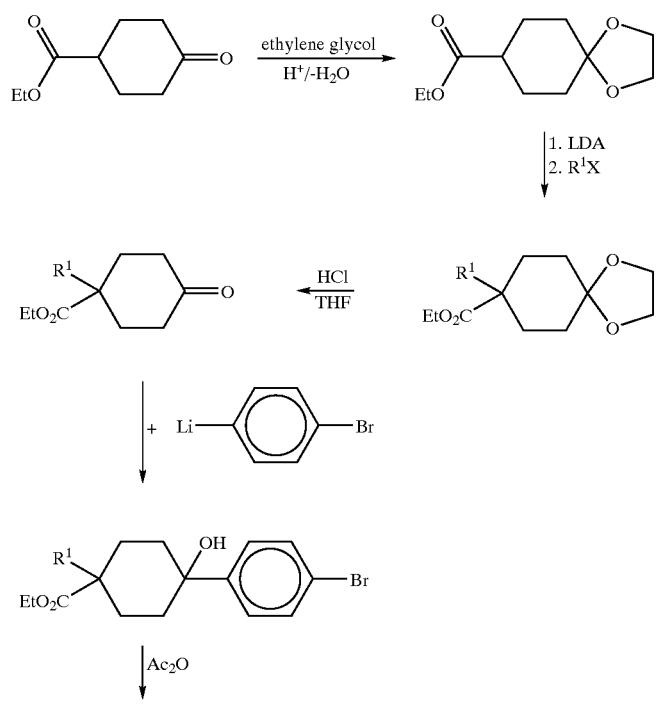

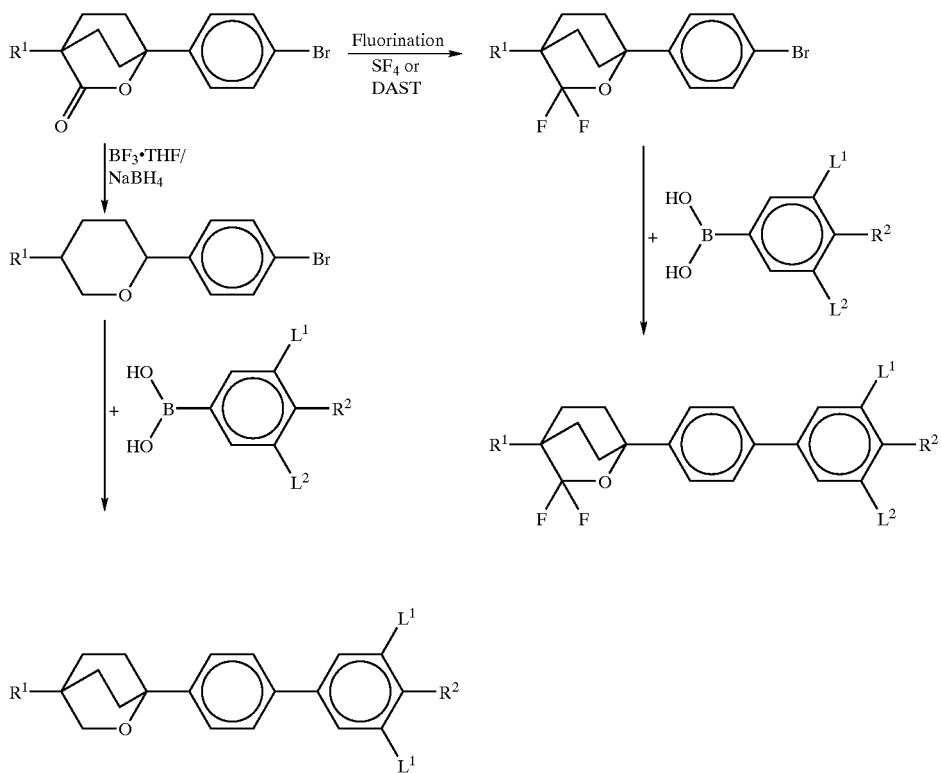
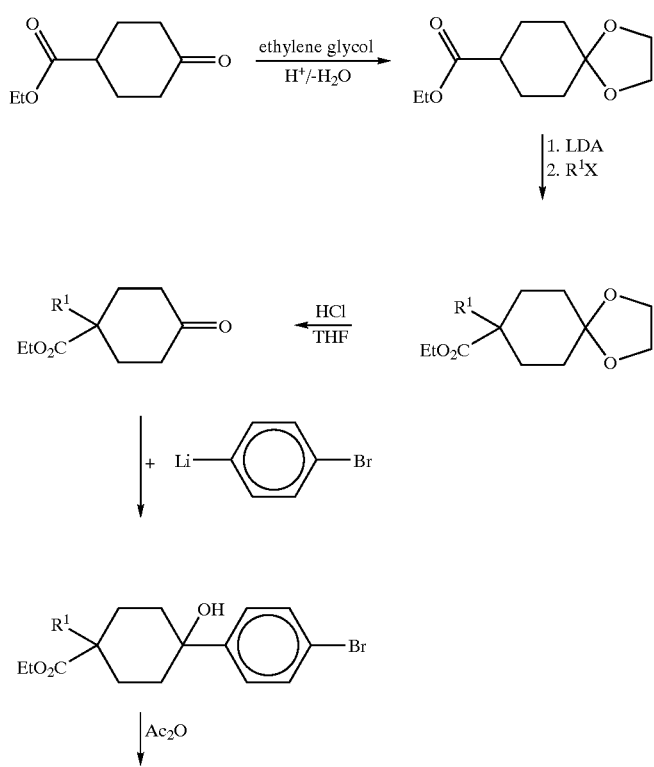
Scheme 2

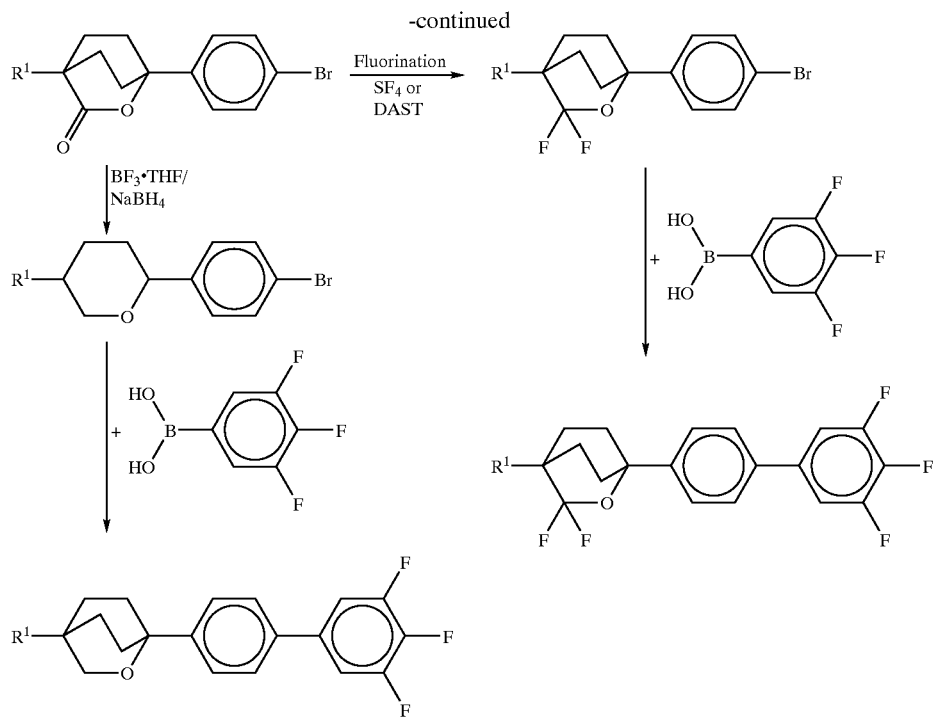

Prior to carrying out the boronic acid coupling, a hydrogenation of the aromatic ring can be performed.

The liquid-crystalline media according to the invention preferably, in addition to one or more oxabicyclooctanes according to the invention, comprise from 2 to 40, particularly from 4 to 30 components as further constituents. Most especially preferably, these media, in addition to one or more oxabicyclooctanes according to the invention, comprise from 7 to 25 components. These further constituents are preferably selected from nematic or nematogenic (monotropic or isotropic) substances, especially substances from the classes of the biphenyls, terphenyls, phenyl benzoates or cyclohexyl benzoates, phenyl or cyclohexyl esters of cyclohexanecarboxylic acid, phenyl or cyclohexyl esters of cyclohexylcyclohexanecarbonic acid, cyclohexylphenyl ester of benzoic acid, of cyclohexanecarbonic acid or cyclohexylcyclohexanecarbonic acid, phenylcyclohexanes, cyclohexylbiphenyls, phenylcyclohexylcyclobenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2(4-phenyl-cyclohexyl) ethanes, 1-cyclohexyl-2-biphenylethanes, 1-phenyl-2-cyclohexylphenylethanes and tolanes. The 1,4-phenylene groups in these compounds can also be fluorinated.

The most important compounds potentially suitable as additional constituents of media according to the invention can be characterized by the formulae II, III, IV, V and VI:

| R'—L—E—R" | II |
| R'—L—COO—E—R" | III |
| R'—L—OOC—E—R" | IV |
| R'—L—CH$_2$CH$_2$—E—R" | V |
| R'—L—C≡C—E—R" | VI |

L and E, which can be identical or different, in the formulae II, III, IV, V and VI, each, independently of one another, are a bivalent radical from the group formed by -Phe-, -Cyc-, -Phe-Phe-, -Phe-Cyc-, -Cyc-Cyc-, -Pyr-, -Dio-, -G-Phe- and -G-Cyc- and mirror images thereof, where Phe is 1,4-phenylene which is unsubstituted or substituted by fluorine, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)-ethyl, pyrimidine-2,5-diyl, pyridine-2,5-diyl or 1,3-dioxane-2,5-diyl.

Preferably, one of the radicals L and E is Cyc, Phe or Pyr. E is preferably Cyc, Phe or Phe-Cyc. Preferably, the media according to the invention comprise one or more compounds selected from the compounds of the formulae II, III, IV, V and VI, in which L and E are selected from the group consisting of Cyc, Phe and Pyr, and at the same time one or more components selected from the compounds of the formulae II, III, IV, V and VI in which one of the radicals L and E is selected from the group consisting of Cyc, Phe and Pyr, and the other radical is selected from the group consisting of -Phe-Phe-, -Phe-Cyc-, -Cyc-Cyc-, -G-Phe- and -G-Cyc-, and optionally one or more components selected from the compounds of the formulae II, III, IV, V and VI, in which the radicals L and E are selected from the group consisting of -Phe-Cyc-, -Cyc-Cyc-, -G-Phe- and -G-Cyc-.

In the compounds of the subformulae IIa, IIIa, IVa, Va and VIa, R' and R" each, independently of one another, are alkyl, alkenyl, alkoxy, alkenyloxy or alkanoyloxy having 1 to 8 carbon atoms. In most of these compounds, R' and R" differ from one another, one of these radicals usually being alkyl or alkenyl. In the compounds of the subformulae IIb, IIIb, IVb, Vb and VIb, R" is —CN—, —CF$_3$, —OCF$_3$, —OCHF$_2$, —F, —Cl or —NCS; R' here has the meanings specified for the compounds of subformulae IIa and VIa and is preferably alkyl or alkenyl. Particularly preferably, R" is selected from the group consisting of —F, —Cl, —CF$_3$, —OCHF$_2$ and —OCF$_3$. Other variants of the designated substituents in the compounds of the formulae II, III, IV, V and VI are also commonly used, however. Many substances or alternatively mixtures can be obtained in accordance with methods known from the literature or in analogous ways.

The media according to the invention, in addition to components from the group consisting of the compounds IIa, IIIa, IVa, Va and VIa (group 1) also comprise components from the group consisting of the compounds IIb, IIIb, IVb, Vb and VIb (group 2), whose proportions are preferably as follows:

Group 1: from 20 to 90%, in particular from 30 to 90%,
Group 2: from 10 to 80%, in particular from 10 to 50%,
the sum of the proportions of the compounds according to the invention and of the compounds from groups 1 and 2 being up to, 100%.

The media according to the invention preferably comprise from 1 to 40%, especially preferably from 5 to 30% of compounds according to the invention, for example, the oxabicyclooctanes of formula I. Also preferred are media comprising more than 40%, in particular from 45 to 90%, of compounds according to the invention. The media preferably comprise from one to five compounds according to the invention.

The preparation of the liquid-crystalline mixtures which can be used according to the invention is effected in a manner customary per se. Generally, the desired quantity of the components used in smaller amounts is dissolved in the components making up the principal constituent, expediently at elevated temperature. It is also possible to mix solutions of the components in an organic solvent, for example in acetone, chloroform or methanol, and to remove the solvent again after thorough mixing, for example by distillation. It is also possible to prepare the mixtures in other conventional ways, for example by using premixtures, for example homolog mixtures, or using so-called "multi-bottle" systems.

The dielectrics may also comprise further additives known to those skilled in the art and described in the literature. For example, from 0 to 15 wt %, preferably from 0 to 10 wt %, of pleochroic dyes and/or chiral dopants can be added. The additives are each employed in concentrations of from 0.01 to 6 wt %, preferably from 0.1 to 3 wt %. However, the concentration data for the other constituents of the liquid-crystal mixtures, i.e. of the liquid-crystalline or mesogenic compounds, are given without taking into account the concentrations of these additives.

In the present application and in the examples below, the structures of the liquid-crystal compounds are indicated by means of acronyms, the transformation into chemical formulae being effected in accordance with tables A and B below. All the radicals $C_nH_{2n+1}$ and $C_mH_{2m+1}$ are straight-chain alkyl radicals having n and m C atoms, respectively. n and m are integers, preferably 1, 2, 3, 4, 5, 6, 7, 8, 9, 10, 11 and 12, with the options of n=m or n≠m. The coding in table B is self-evident. In table A, only the acronym for the parent structure is given. In individual cases, the acronym for the parent structure is followed, separated by a hyphen, by a code for the substituents $R^1$, $R^2$, $L^1$ and $L^2$:

| Code for $R^1$ $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| nN | $C_nH_{2n+1}$ | CN | H | H |
| nN.F | $C_nH_{2n+1}$ | CN | H | F |
| nF | $C_nH_{2n+1}$ | F | H | H |

-continued

| Code for $R^1$ $R^2$, $L^1$, $L^2$ | $R^1$ | $R^2$ | $L^1$ | $L^2$ |
|---|---|---|---|---|
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nOCF$_2$ | $C_nH_{2n+1}$ | NCS | H | H |
| rVsN | $C_rH_{2r+1}$—CH=CH—$C_sH_{2s}$— | CN | H | H |
| V-T | CH$_2$=CH | CF$_3$ | H | H |
| V2-T | CH$_2$—CH—C$_2$H$_4$ | CF$_3$ | H | H |
| 1V-OT | CH$_3$—CH=CH | OCF$_3$ | H | H |
| rEsN | $C_rH_{2r+1}$—O—$C_sH_{2s}$— | CN | H | H |
| nAm | $C_nH_{2n+1}$ | COOC$_m$H$_{2m+1}$ | H | H |
| nOCCF$_2$.F.F | $C_nH_{2n+1}$ | OCH$_2$CF$_2$H | F | F |

Preferred mixture components are shown in tables A and B, where $R^1$, $R^2$, $L^1$ and $L^2$ can have the meanings specified in the table above.

TABLE A

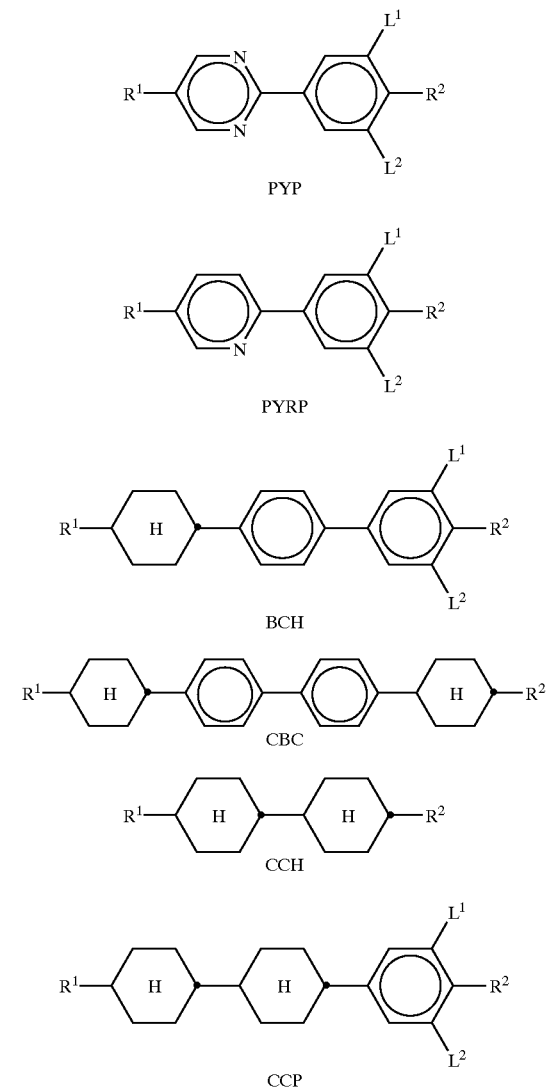

TABLE A-continued
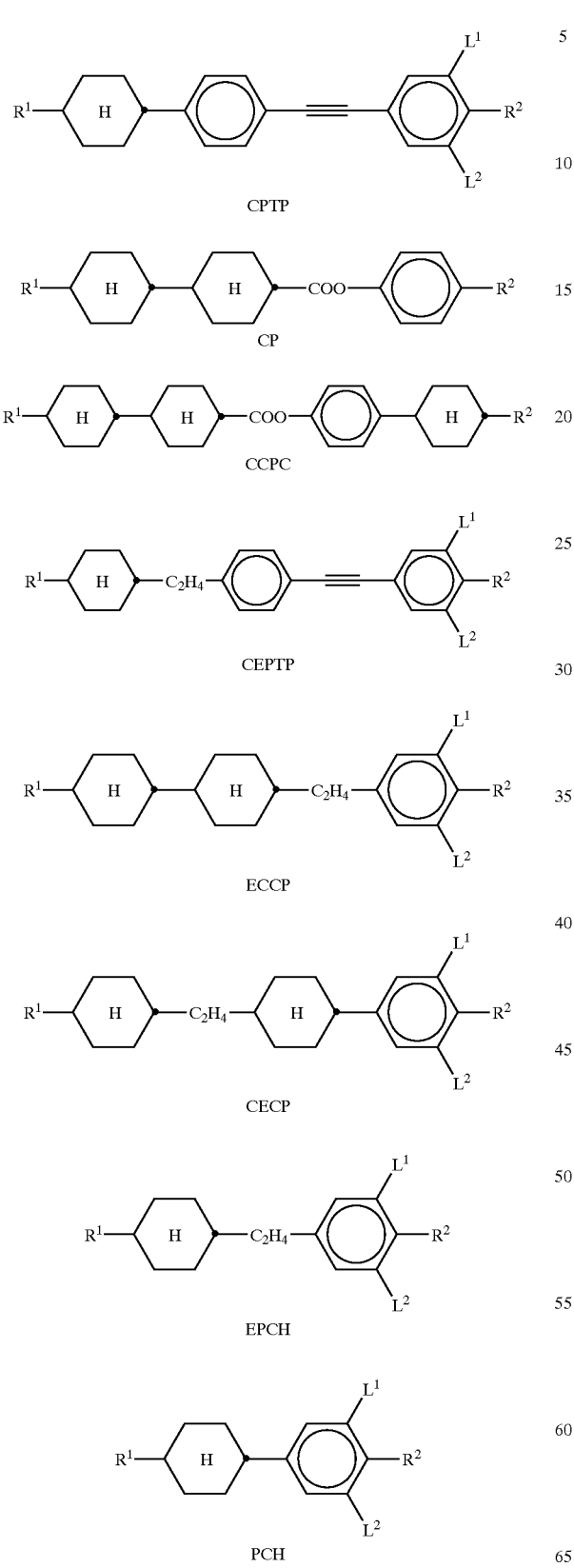
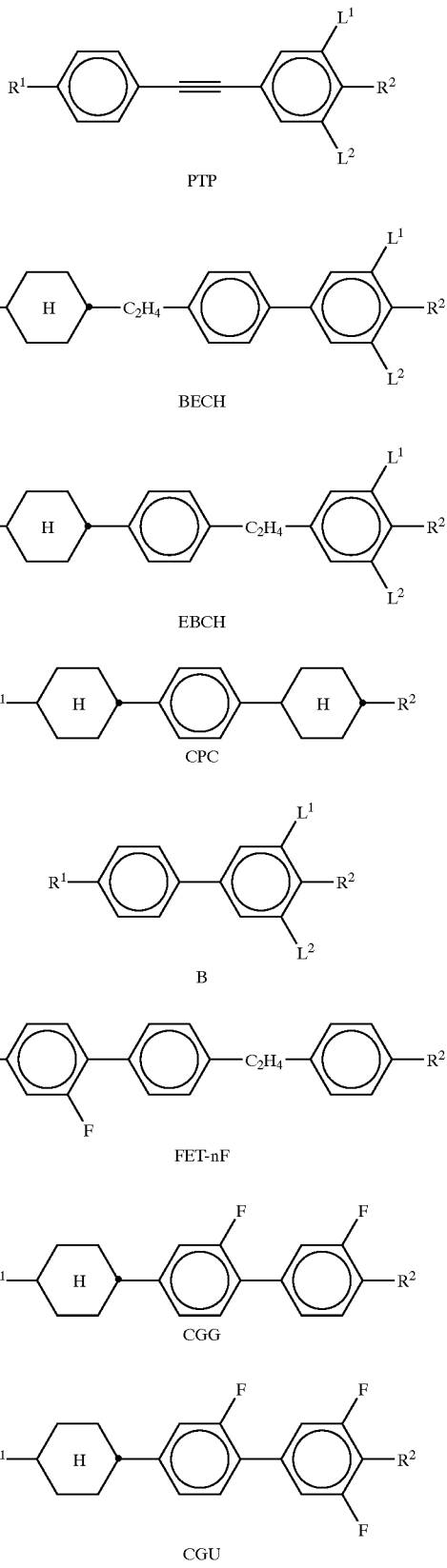

TABLE A-continued
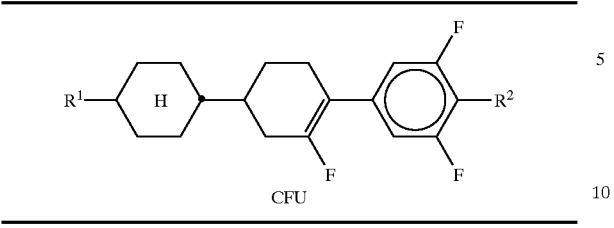
CFU
TABLE B
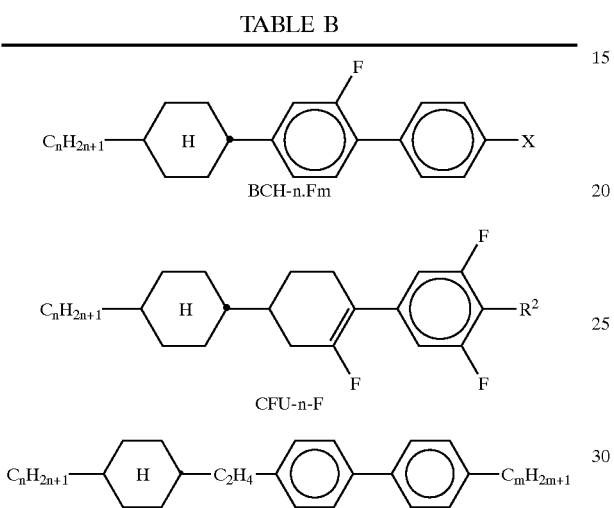
BCH-n.Fm
CFU-n-F
Inm
CBC-nmF
ECCP-nm
CCH-n1EM
OS-nm
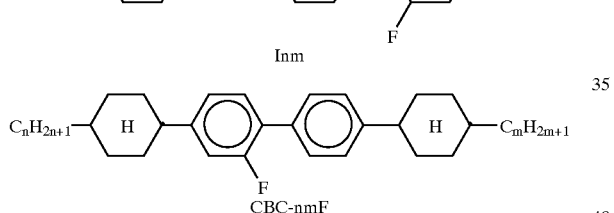
CCZU-n-F
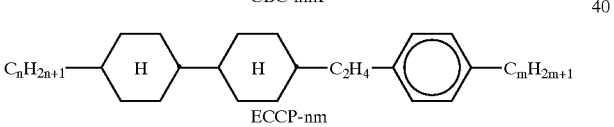
CH-nm
TABLE B-continued
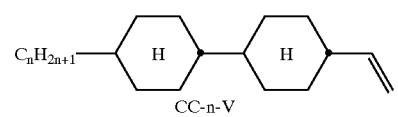
CC-n-V
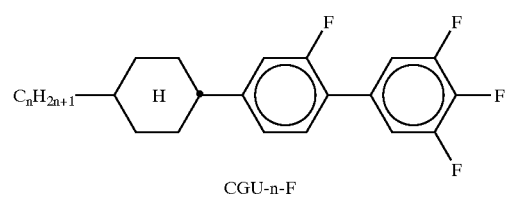
CGU-n-F
CDU-n-F
DCU-n-F
CGG-n-F
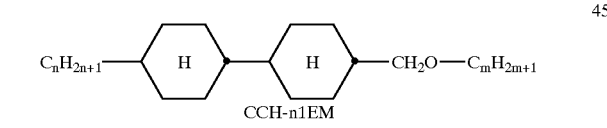
CDU-n-OD
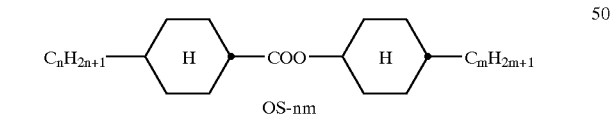
CC-n-OT
CCH-nCF$_3$
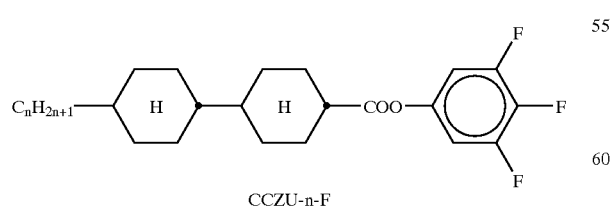
ECCH-nCF$_3$
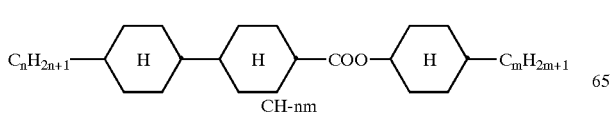
DC-n-T

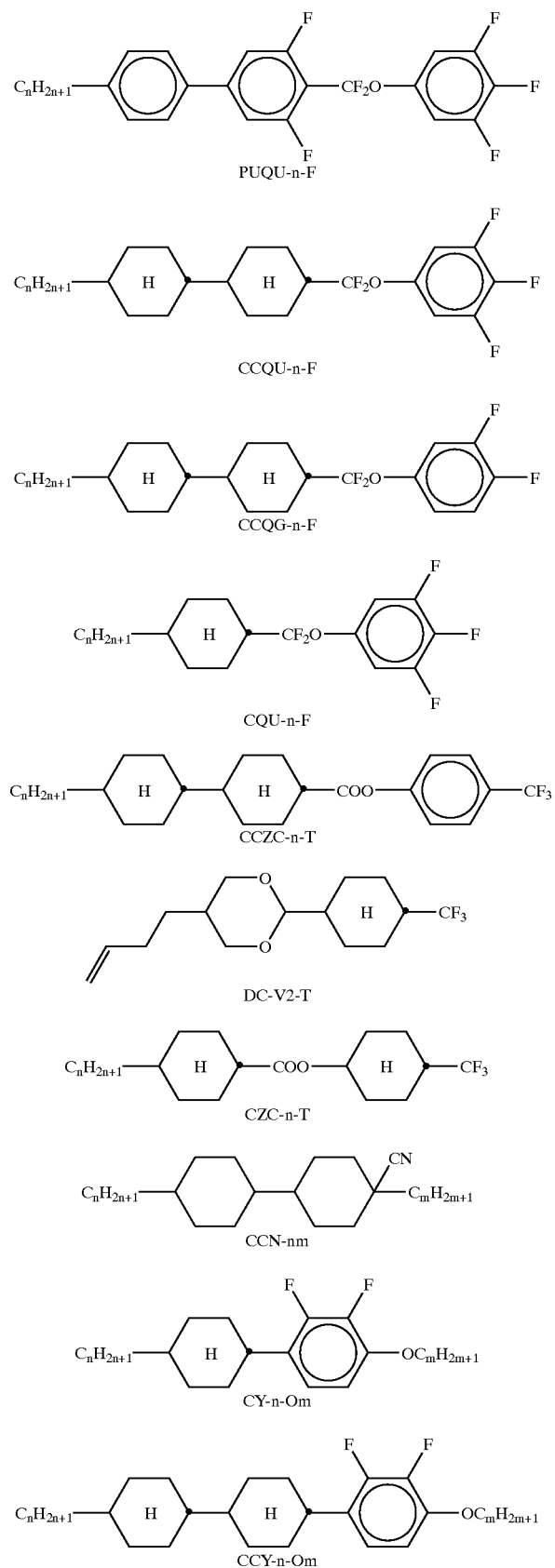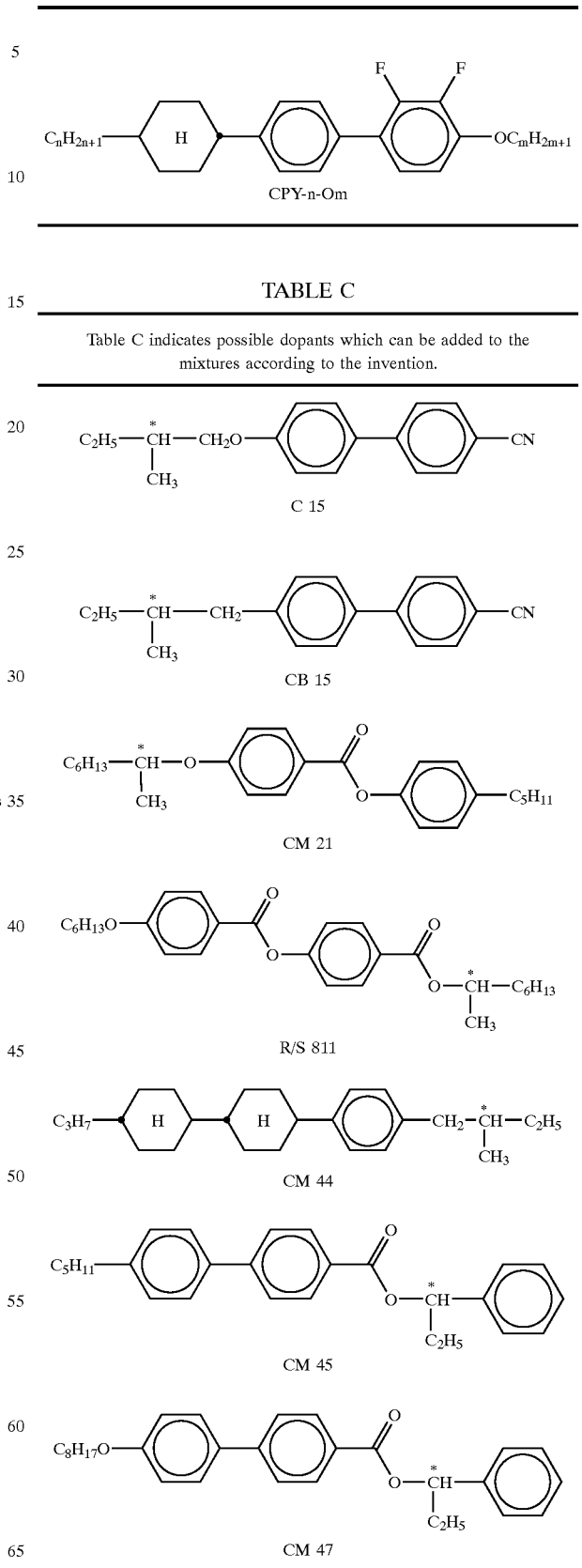

TABLE C-continued

Table C indicates possible dopants which can be added to the mixtures according to the invention.

TABLE D

Stabilizers which can be added, for example, to the mixtures according to the invention are shown below.

TABLE D-continued

Stabilizers which can be added, for example, to the mixtures according to the invention are shown below.

TABLE D-continued
Stabilizers which can be added, for example, to the mixtures according to the invention are shown below.
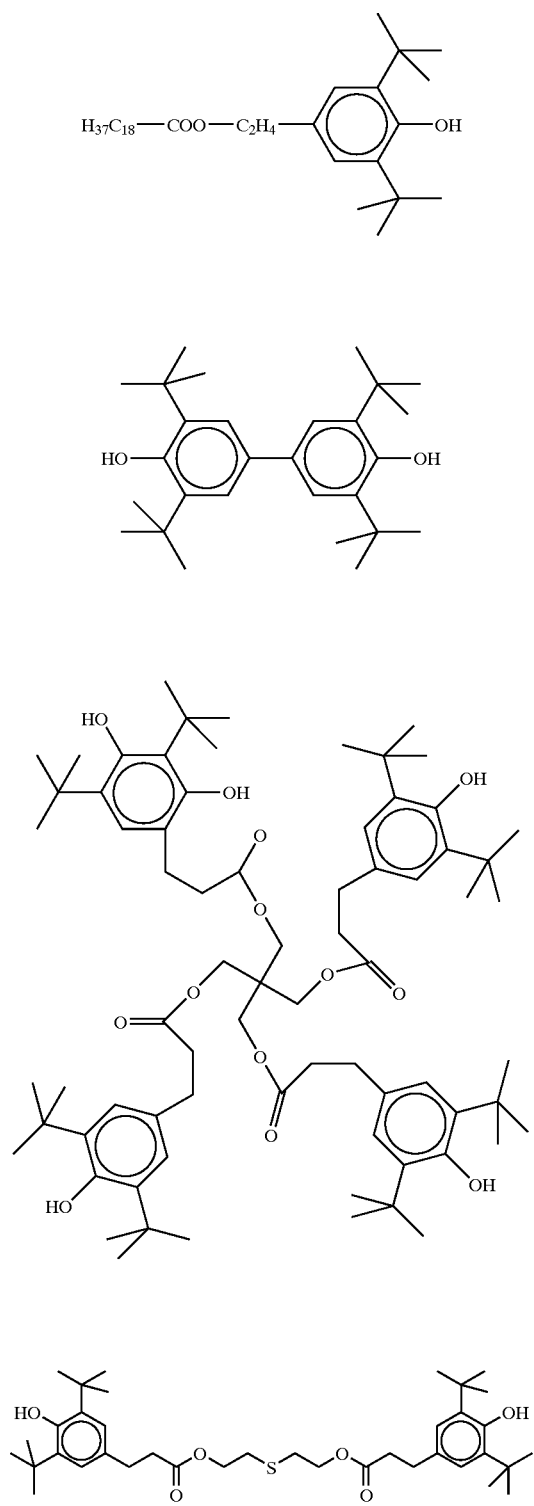
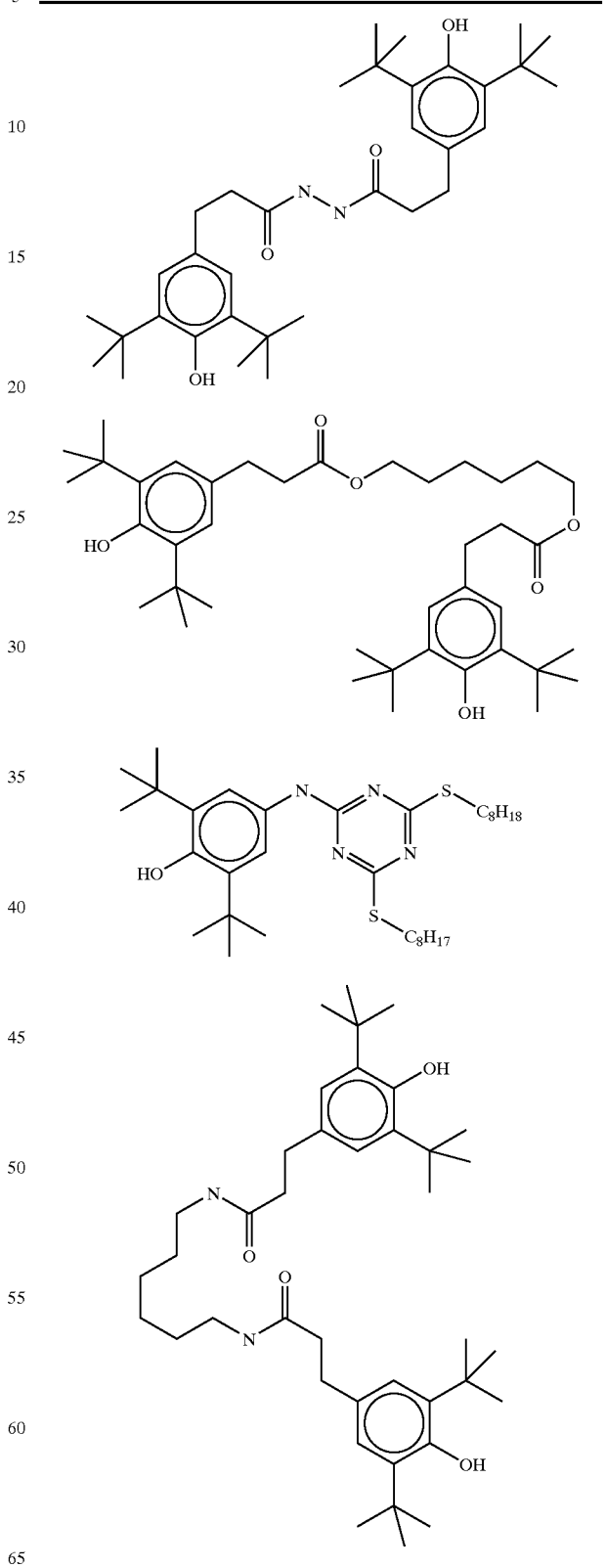

TABLE D-continued
Stabilizers which can be added, for example, to the mixtures according to the invention are shown below.
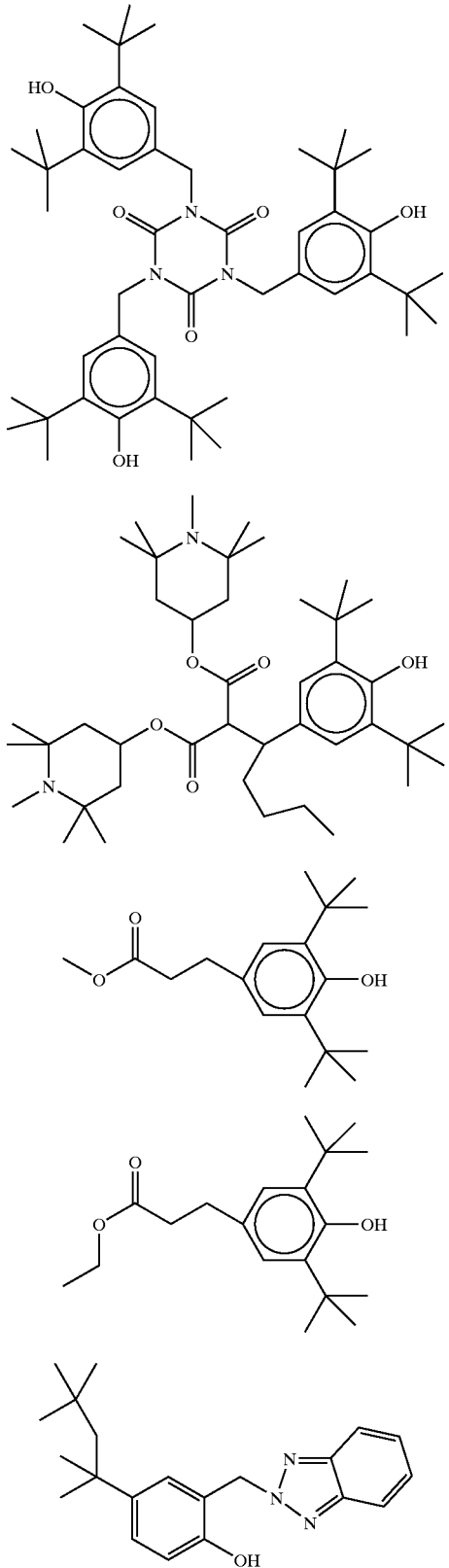
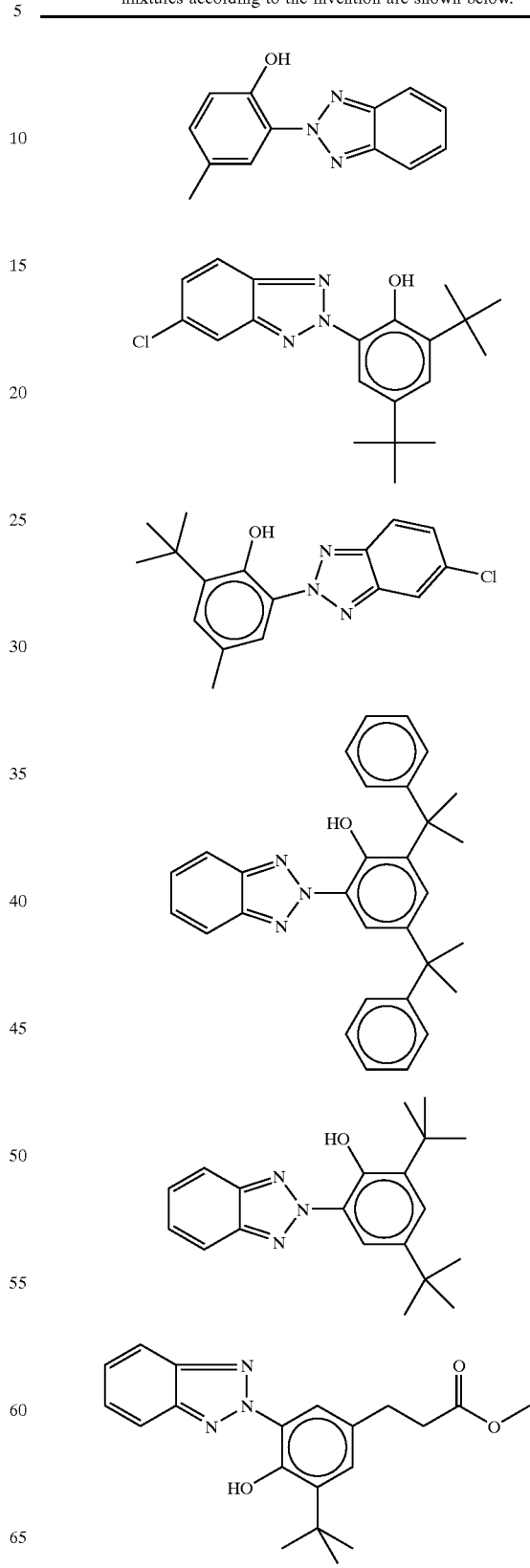

TABLE D-continued

Stabilizers which can be added, for example, to the mixtures according to the invention are shown below.

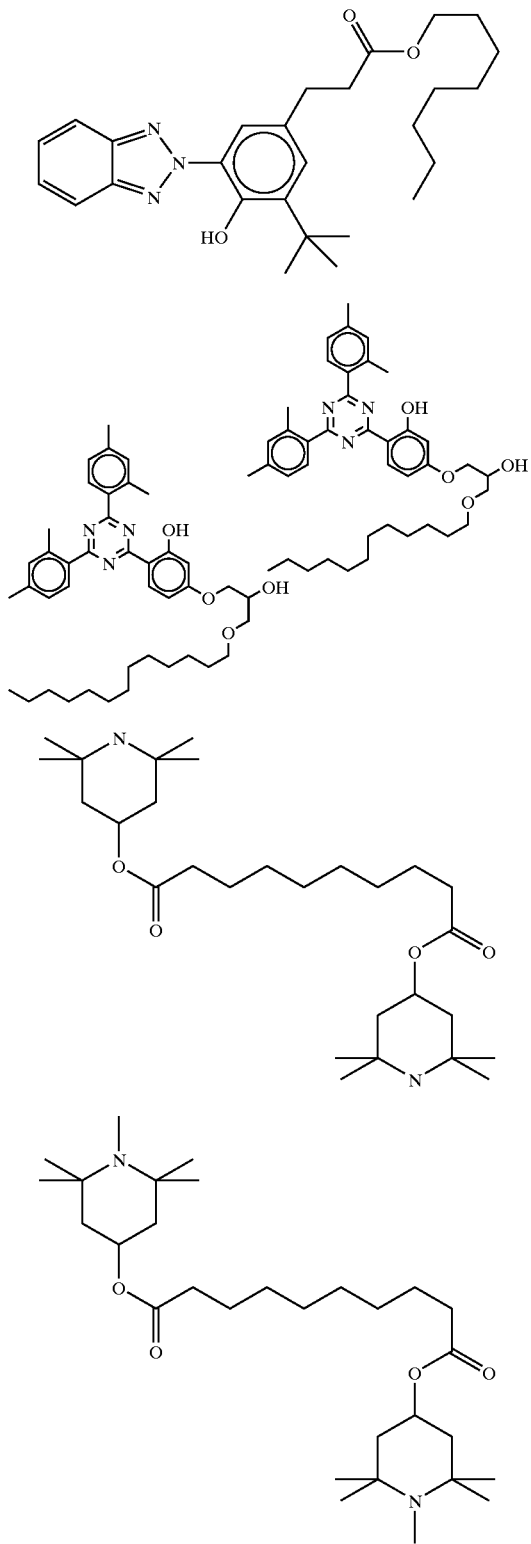

The entire disclosure of all applications, patents and publications, cited above and below, and of corresponding German Application No. 10148485.2, filed Oct. 1, 2001, is hereby incorporated by reference.

EXAMPLES

In the foregoing and in the following examples, all temperatures are set forth uncorrected in degrees Celsius; and, unless otherwise indicated, all parts and percentages are by weight.

The following examples are intended to illustrate the invention without limiting it. Hereinabove and hereinafter, percentages are percent by weight. All temperatures are given in centigrade. Fp means fusion point, Cp means clearing point. In addition, C=crystalline state, N=nematic phase, S=smectic phase and I=isotropic phase. The data between these symbols represent the transition temperatures. An means optical anisotropy (589 nm, 20° C.), the flow viscosity (mm²/sec) was determined at 20° C. The rotational viscosity $\gamma_1$ (mPa.s) was likewise determined at 20° C.

"Usual work-up" means: water is added if required, followed by extraction with dichloromethane, diethyl ether, methyl t-butyl ether or toluene, phase separation, drying of the organic phase, evaporation and purification of the product by distillation under reduced pressure or crystallization and/or chromatography. The following abbreviations are used:

| | |
|---|---|
| n-BuLi | 1.6 molar solution of n-butyllithium in n-hexane |
| DMAP | 4-(dimethylamino)-pyridine |
| THF | tetrahydrofuran |
| DCC | N,N'-dicyclohexylcarbodiimide |
| LDA | lithium dimethylamide |

Synthesis Examples 1 to 9

Example 1

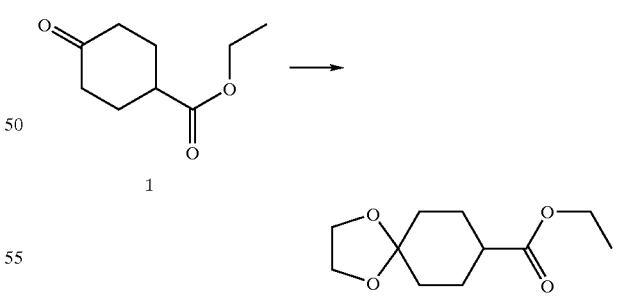

2.4 mol of ethyl 4-oxocyclohexanecarboxylate, 120 mmol of toluene-4-sulfonic acid monohydrate, 3.6 mmol of ethylene glycol and 1500 ml of toluene are heated and boiled on a water trap. The mixture is allowed to cool to room temperature, washed with 5% strength NaHCO₃ solution and then with water, the organic phase is dried and boiled down on a rotary evaporator.

Example 2

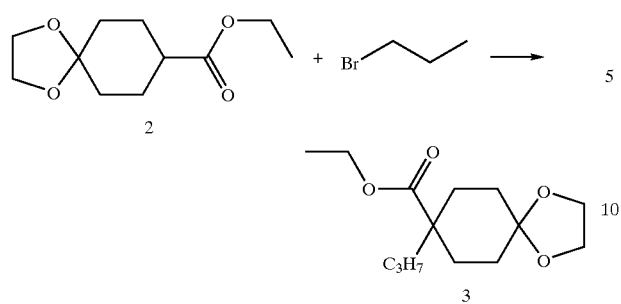

In a nitrogen atmosphere, 1400 ml of THF are introduced as the initial charge, cooled to −20° C., and 2.424 mol of butyllithium as a 15% strength solution in THF are added dropwise at −20° to −30° C. The mixture is then cooled to −70° C., followed by the successive dropwise addition of 2.42 mol of diisopropylamine, 1.865 mol of 2 in 400 ml of THF and 2.42 mol of 1-bromopropane. The mixture is then stirred for a further 12 h at room temperature. The solution obtained is poured into 5 l of 1N HCl. The organic phase is separated, dried and boiled down on a rotary evaporator, affording an orange-yellow oil.

Example 3

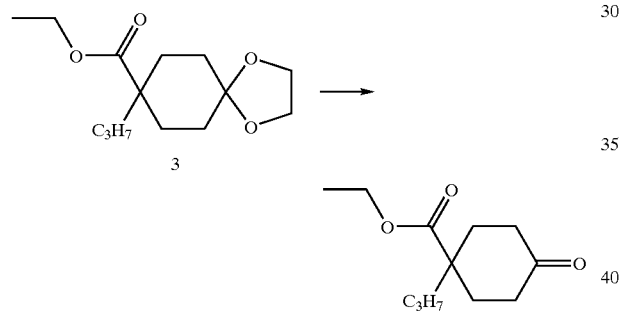

1.506 mol of 3, 761.5 ml of 2N HCl and 700 ml of THF are introduced as the initial charge and heated to boiling point (70° C.). The mixture is stirred for 6 h under reflux, 50 ml of concentrated HCl is added, followed by stirring under reflux for a further 12 h. Then the water phase is separated, extracted with methyl t-butyl ether, and the combined organic phases are extracted with saturated $NaHCO_3$ solution, dried and boiled down on a rotary evaporator, affording an orange-yellow oil. This is distilled at 0.02–0.03 mbar on a 30 cm Vigreux column.

Example 4

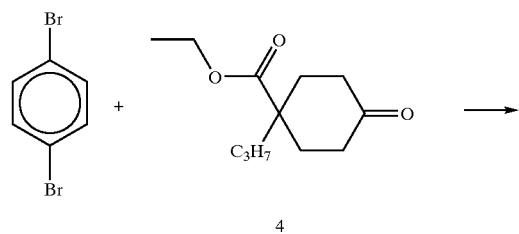

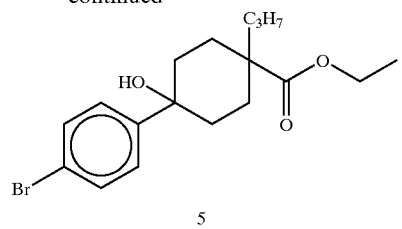

Under nitrogen atmosphere, 0.2 mol of 1,4-dibromobenzene in 300 ml of diethyl ether are introduced as the initial charge and cooled to −50° C. At −50 to −40° C., 0.2 mol of butyllithium as a 15% strength solution in hexane is added dropwise. The mixture is then warmed to −20° C., and 0.2 mol of 4 in 50 ml of diethyl ether is added dropwise. The mixture is stirred at −20° C. for a further 1 h, warmed to 0° C., hydrolyzed with water and acidified with concentrated HCl. The organic phase is separated off, dried and boiled down on a rotary evaporator, affording a pale yellowish, viscous oil.

Example 5

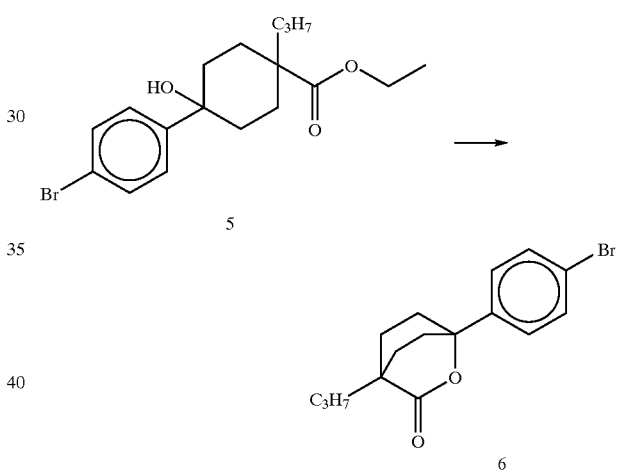

0.044 mol of 5 is dissolved in 500 ml of acetic anhydride and stirred overnight under reflux. Acetic anhydride is then stripped off under reduced pressure. The crude product is chromatographed over silica gel, first with dichloromethane/hexane 2:1 and then with pure dichloromethane. Removal of the solvent on a rotary evaporator affords a pale yellowish oil which is recrystallized from 72.5 ml of ethanol. Crystals are formed which are filtered off with suction at 2° C., washed and dried.

Example 6

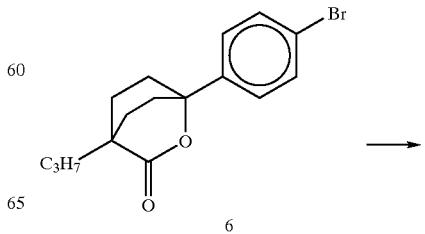

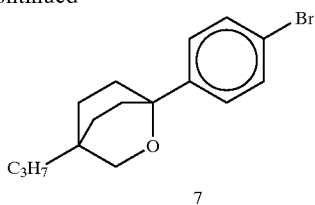

7

Under a nitrogen atmosphere, 82.311 mmol of 6 dissolved in 170 ml of THF are introduced as the initial charge, and 304.549 mmol of boron trifluoride. THF are added dropwise at 20 to 22° C. The mixture is stirred for a further 30 min at this temperature, followed by dropwise addition of a solution of 205.777 mmol of sodium borohydride in 250 ml of diethylene glycol dimethyl ether. The mixture is stirred for a further 2 h at room temperature, and the solution obtained is poured onto a mixture of 400 ml of ice water and 200 ml of methyl t-butyl ether. The organic phase is separated off, dried and boiled down on a rotary evaporator. The residue is separated chromatographically with dichloromethane on silica gel as the stationary phase. Removal of the solvent on a rotary evaporator affords a yellow oil which is recrystallized from methanol. The crystals are filtered off with suction at 2° C., washed and dried.

Example 7

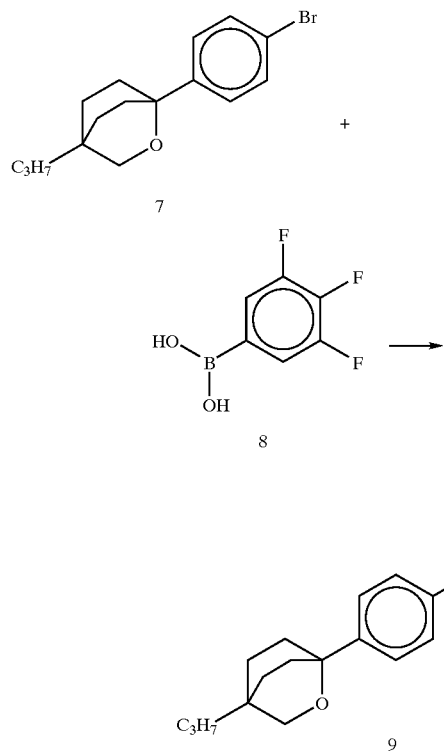

7.982 mmol of sodium metaborate octahydrate are introduced as the initial charge in 5 mml of water, and 0.213 mol of bis(triphenylphosphine)-palladium(II) chloride, 0.213 mmol of hydrazinium hydroxide and 10.643 mmol of 7 are then added successively. This is followed by the addition of 10.643 mmol of 8 dissolved in 12 ml of THF. The mixture is heated to boiling and stirred for 4 h. The aqueous phase is separated off, the organic phase is dried and boiled down on a rotary evaporator. The residue is chromatographically separated over silica gel, using dichloromethane/hexane 1:1. Removal of the solvent on a rotary evaporator leaves colorless crystals. These are recrystallized from 31.5 ml of ethanol and filtered off with suction at about 2° C., followed by further recrystallization from 8.2 ml of hexane/ethanol 1:1. The crystals are filtered off with suction at 5° C., washed with hexane and dried.

Example 8

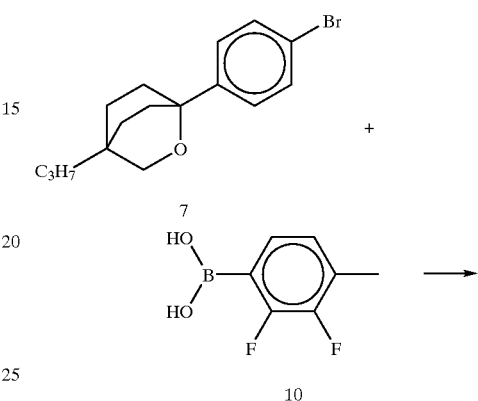

8.250 mmol of sodium metaborate octahydrate are introduced as the initial charge in 5 ml of water, and 0.22 mmol of bis(triphenylphosphine)-palladium(II) chloride, 0.22 mmol of hydrazinium hydroxide and 11 mmol of 7 are then added successively. This is followed by the addition of 11 mmol of 10 dissolved in 12.5 ml of THF. The mixture is heated to boiling and stirred for 4 h. The aqueous phase is separated off, the organic phase is dried and boiled down on a rotary evaporator. The residue is chromatographically separated over silica gel, using dichloromethane/hexane 1:1. Removal of the solvent on a rotary evaporator leaves colorless crystals. These are recrystallized from ethanol and filtered off with suction at about room temperature, followed by further recrystallization from 20 ml of heptane. The crystals are filtered off with suction at 5° C., washed with pentane and dried.

Example 9

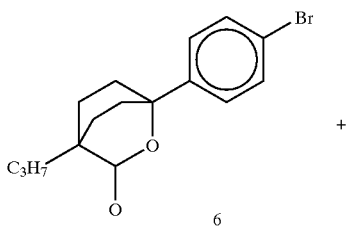

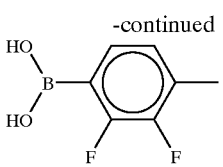

10

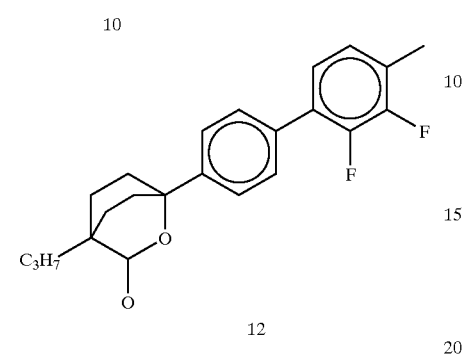

12

16.5 mmol of sodium metaborate octahydrate are introduced as the initial charge in 10 ml of water, and 0.44 mmol of bis(triphenylphosphine)-palladium(II) chloride, 0.44 mmol of hydrazinium hydroxide and 22 mmol of 6 are then added successively. This is followed by the addition of 22 mmol of 10 dissolved in 25 ml of THF. The mixture is heated to boiling and stirred for 4 h. The aqueous phase is separated off, the organic phase is dried and boiled down on a rotary evaporator. The residue is chromatographically separated over silica gel, using dichloromethane/hexane 2:1. Removal of the solvent on a rotary evaporator leaves colorless crystals. These are recrystallized from 100 ml of ethanol, and the crystals are filtered with suction at 10° C.

Example 10

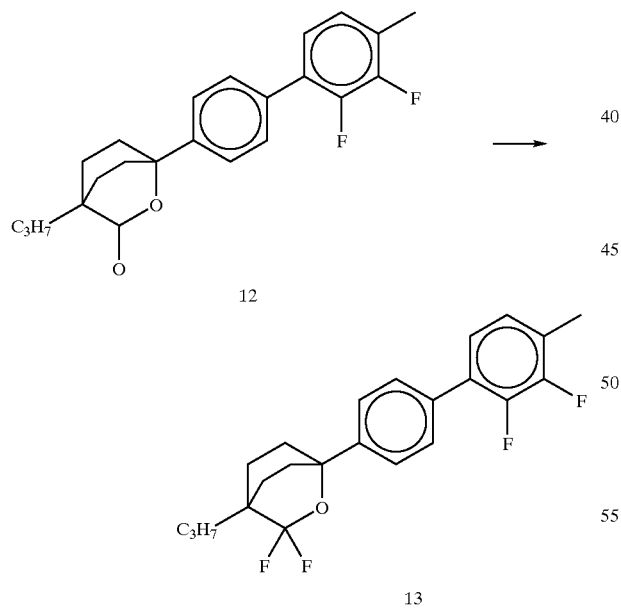

12

13

10 mmol of 12 are heated to 80° C. for 5 h in 50 ml of diethylaminosulfur trifluoride (DAST) and are worked up in the customary manner.

Yield: 5.5 mmol of 13 (55% of theory)

Comparative Example

Below, the compounds 9 and 11, respectively, are compared with the corresponding prior art compounds 9' and 11', respectively, which instead of the oxabicyclooctanediyl group have a trans-1,4-cyclohexylene group.

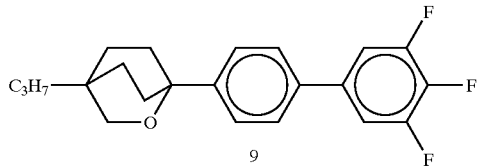

9

Clearing point: 83.6° C.
$\Delta\epsilon$ [1 kHz, 20° C.]: 15.9
$\Delta n$ [589 nm, 20° C.]: 0.1472

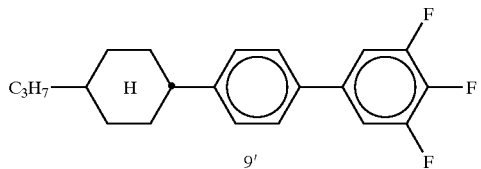

9'

Clearing point: 54.8° C.
$\Delta\epsilon$ [1 kHz, 20° C.]: 12.6
$\Delta n$ [589 nm, 20° C.]: 0.1420

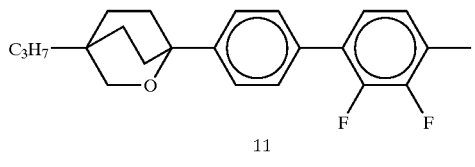

11

Clearing point: 176° C.
$\Delta\epsilon$ [1 kHz, 20° C.]: −1.0
$\Delta n$ [589 nm, 20° C.]: 0.1398

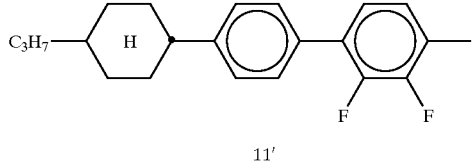

11'

Clearing point: 145.7° C.
$\Delta\epsilon$ [1 kHz, 20° C.]: −2.2
$\Delta n$ [589 nm, 20° C.]: 0.1567

The compound 9 according to the invention, compared with the reference compound 9', while having a comparable value for the birefringence $\Delta n$ has a distinctly higher clearing point and a distinctly higher dielectric anistropy $\Delta\epsilon$.

The compound 11 according to the invention, compared with the reference compound 11', while having a comparable value for the dielectric anisotropy $\Delta\epsilon$ has a distinctly higher clearing point and a distinctly lower birefringence $\Delta n$.

Mixture Examples A–G

EXAMPLE A

| Component | [%] | | |
|---|---|---|---|
| BCH-3F.F | 10.80 | Clearing point | +91.7° C. |
| BCH-5F.F | 9.00 | $\Delta n$ [589 nm, 20° C.]: | +0.1018 |
| ECCP-3OCF$_3$ | 4.50 | $\Delta\epsilon$ [1 kHz, 20° C.]: | +6.4 |
| ECCP-5OCF$_3$ | 4.50 | | |

-continued

| Component | [%] |
|---|---|
| CBC-33F | 1.80 |
| CBC-53F | 1.80 |
| CBC-55F | 1.80 |
| PCH-6F | 7.20 |
| PCH-7F | 5.40 |
| CCP-2OCF$_3$ | 7.20 |
| CCP-3OCF$_3$ | 10.80 |
| CCP-4OCF$_3$ | 6.30 |
| CCP-5OCF$_3$ | 9.90 |
| PCH-5F | 9.00 |
| Compound 9 | 10.00 |

EXAMPLE B

| Component | [%] | | |
|---|---|---|---|
| BCH-3F.F | 10.90 | Clearing point: | +91.8° C. |
| BCH-5F.F | 9.09 | $\gamma_1$ [20° C., mPa.s]: | 151 |
| ECCP-3OCF$_3$ | 4.54 | | |
| ECCP-5OCF$_3$ | 4.54 | | |
| CBC-33F | 1.82 | | |
| CBC-53F | 1.82 | | |
| CBC-55F | 1.82 | | |
| PCH-6F | 7.27 | | |
| PCH-7F | 5.45 | | |
| CCP-3OCF$_3$ | 7.27 | | |
| CCP-3OCF$_3$ | 10.90 | | |
| CCP-4OCF$_3$ | 6.36 | | |
| CCP-5OCF$_3$ | 10.00 | | |
| PCH-5F | 9.09 | | |
| Compound 9 | 9.13 | | |

EXAMPLE C

| Component | [%] | | |
|---|---|---|---|
| BCH-3F.F | 11.39 | Clearing point | +96.8° C. |
| BCH-5F.F | 9.49 | $\gamma_1$ [20° C., mPa.s]: | 144 |
| ECCP-3OCF$_3$ | 4.75 | | |
| ECCP-5OCF$_3$ | 4.75 | | |
| CBC-33F | 1.90 | | |
| CBC-53F | 1.90 | | |
| CBC-55F | 1.90 | | |
| PCH-6F | 7.59 | | |
| PCH-7F | 5.70 | | |
| CCP-2OCF$_3$ | 7.59 | | |
| CCP-3OCF$_3$ | 11.39 | | |
| CCP-4OCF$_3$ | 6.65 | | |
| CCP-5OCF$_3$ | 10.44 | | |
| PCH-5F | 9.49 | | |
| Compound 11 | 5.07 | | |

EXAMPLE D

| Component | [%] | | |
|---|---|---|---|
| BCH-3F.F | 11.40 | Clearing point: | +96.7° C. |
| BCH-5F.F | 9.50 | $\Delta n$ [589 nm, 20° C.]: | +0.1001 |
| ECCP-3OCF$_3$ | 4.75 | $\Delta \epsilon$ [1 kHz, 20° C.]: | +5.0 |
| ECCP-5OCF$_3$ | 4.75 | $\nu$ [20° C., mm$^2$s$^{-1}$]: | 17 |
| CBC-33F | 1.90 | | |
| CBC-53F | 1.90 | | |
| CBC-55F | 1.90 | | |

| Component | [%] |
|---|---|
| PCH-6F | 7.60 |
| PCH-7F | 5.70 |
| CCP-2OCF$_3$ | 7.60 |
| CCP-3OCF$_3$ | 11.40 |
| CCP-4OCF$_3$ | 6.65 |
| CCP-5OCF$_3$ | 10.45 |
| PCH-5F | 9.50 |
| Compound 9 | 5.00 |

EXAMPLE E

| Component | [%] | | |
|---|---|---|---|
| PCH-301 | 9.53 | Clearing point: | +85.3° C. |
| PCH-302 | 9.53 | $\Delta \epsilon$ [1 kHz, 20° C.]: | −1.4 |
| CCH-301 | 31.45 | | |
| CCN-47 | 10.48 | | |
| CCN-55 | 9.53 | | |
| CBC-33F | 4.76 | | |
| CBC-53F | 4.76 | | |
| CBC-55F | 4.76 | | |
| CBC-33 | 4.76 | | |
| CBC-53 | 5.72 | | |
| Compound 11 | 4.71 | | |

EXAMPLE F

| Component | [%] | | |
|---|---|---|---|
| CY-3-O4 | 8.00 | Cp. [° C.]: | +80.0 |
| CY-5-O2 | 20.00 | $\Delta n$ [589 nm, 20° C.]: | 0.109 |
| CY-5-O4 | 8.00 | $\Delta \epsilon$ [1 kHz, 20° C.]: | −4.4 |
| CCY-3-O2 | 9.00 | V$_0$: | 2.0 |
| BCH-32 | 3.00 | $\gamma_1$ [mPa.s]: | 183 |
| CPY-2-O2 | 11.00 | | |
| CPY-3-O2 | 13.00 | | |
| CCP-5-V | 15.00 | | |
| CCP-3-V1 | 5.00 | | |
| Compound 11 | 8.00 | | |

EXAMPLE G

| Component | [%] | | |
|---|---|---|---|
| CY-3-O4 | 12.00 | Cp. [° C.]: | +82.0 |
| CY-5-O2 | 20.00 | $\Delta n$ [589 nm, 20° C.]: | 0.109 |
| CCY-3-O2 | 8.00 | $\Delta \epsilon$ [1 kHz, 20° C.]: | −3.9 |
| BCH-32 | 5.00 | V$_0$: | 2.1 |
| CPY-2-O2 | 12.00 | $\gamma_1$ [mPa.s]: | 169 |
| CPY-3-O2 | 12.00 | | |
| CCP-5-V | 18.00 | | |
| CCP-3-V1 | 5.00 | | |
| Compound 11 | 8.00 | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An oxabicyclooctane compound of the formula I

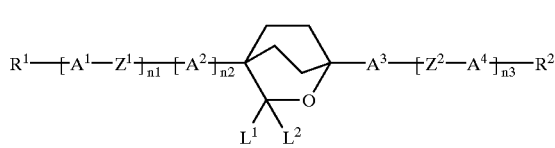

in which

L¹ and L² independently of one another, are H or F, R¹ and R², independently of one another, are CN or halogen or alkyl having from 1 to 12 C atoms which is unsubstituted or mono- to perhalo-substituted by halogen, CN or CF₃, optionally one or more CH₂ groups being replaced, in each case independently of one another, by —O—, —S—, —CO—, —CO—O—, —O—CO—, —O—CO—O—, —CH=CH—, —CH=CF—, —CF=CF—, —C≡C—or 1,3-cyclobutylene in such a way that S and/or O atoms are not linked directly to one another, are, independently of one another: trans-1,4-cyclohexylene, in which one or two nonadjacent CH₂ groups are optionally replaced by —O—, and/or —S—; 1,4-phenylene, in which one or two CH groups are optionally replaced by N; 1,4-cyclohexenylene; 1,4-bicyclo-(2,2,2)-octylene; piperidine-1,4-diyl-; naphthalene-2,6-diyl; decahydronaphthalene-2,6-diyl; or 1,2,3,4-tetrahydronaphthalene-2,6-diyl; where the rings in the above are optionally monosubstituted or polysubstituted by F, Cl, CN, or CF₃, Z¹ and Z² each, independently of one another, are —CH₂O—, —OCH₂—, —CF₂O—, —OCF₂—, —COO—, —OCO—, —CF₂CF₂—, —CH₂CH₂—, —(CH₂)₄—, —(CH₂)₃O—, —O(CH₂)₃—, —CF₂CH₂—, —CH=CH—, —CH=CF—, —CF=CF—, —C≡C— or a single bond, n1 is 0 or 1, n2 is 0 or 1, and n3 is 0, 1 or 2, with the proviso that n1=0, if n2=0.

2. An oxabicyclooctane compound of claim 1, wherein n1=0.

3. An oxabicyclooctane compound of claim 2, wherein n2=0.

4. An oxabicyclooctane compound of claim 1, wherein L¹ and L² are F.

5. An oxabicyclooctane compound of claim 1, wherein L¹ and L² are H.

6. A liquid-crystalline medium comprising at least two liquid-crystalline components, wherein at least one component is an oxabicyclooctane compound of claim 1.

7. An electro-optical display element containing a liquid-crystalline medium as claimed in claim 6.

8. An oxabicyclooctane compound of claim 1, which is of the formula Ia,

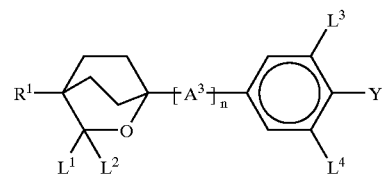

in which

A³ is

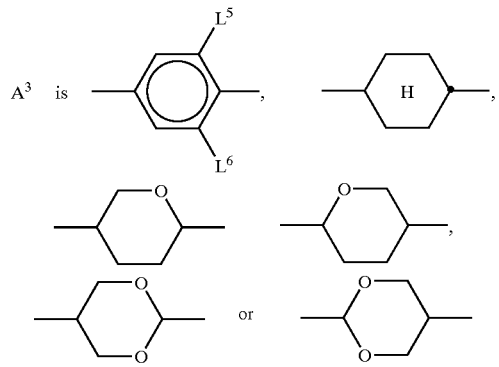

L$^{1-6}$ each, independently of one another, are H or F,

Y is F, Cl, CN or an alkyl or alkoxy radicals having from 1 to 6 C atoms, one or more CH₂ groups in these radicals optionally being replaced by —O— or —CH=CH—, such that O atoms not being linked directly to one another, n is 0 or 1, and R¹ has the meanings specified in claim 1.

9. An oxabicyclooctane compound of claim 8, wherein Y is F, Cl, CN, OCF₃ or OCHF₂.

10. An oxabicyclooctane compound of claim 3 which is of the formula Ib

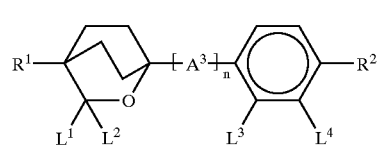

in which

A³ is

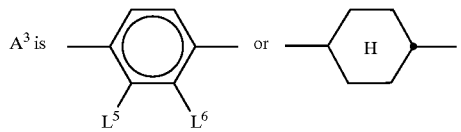

L$^{1-6}$ each, independently of one another, are H or F,

R¹ and R² independently of one another, are CN or halogen or alkyl having from 1 to 12 C atoms which is unsubstituted or mono- to perhalo-substituted by halogen, CN or CF₃, optionally one or more CH₂ groups being replaced, in each case independently of one another, by —O—, —S—, —CO—, —CO—O—, —O—CO—, —O—CO—O—, —CH=CH—, —CH=CF—, —CF=CF—, —C≡C— or 1,3-cyclobutylene in such a way that S and/or O atoms are not linked directly to one another, and n is 0 or 1, with the proviso that at least one of the groups $L_3$, $L^4$, $L^5$ and $L^6$ is F.

11. An oxabicyclooctane compound of claim 10, wherein $R^2$ is straight-chain alkyl or oxaalkyl having from 1 to 8 C atoms or alkenyl or oxaalkenyl having from 2 to 7 C atoms.

12. An oxabicyclooctane compound of claim 8, wherein $L^1$ and $L^2$ are F.

13. An oxabicyclooctane compound of claim 10, wherein $L^1$ and $L^2$ are F.

14. An oxabicyclooctane compound of claim 8, wherein $L^1$ and $L^2$ are H.

15. An oxabicyclooctane compound of claim 10, wherein $L^1$ and $L^2$ are H.

16. A liquid-crystalline medium comprising at least two liquid-crystalline components, wherein at least one component is an oxabicyclooctane compound of claim 8.

17. A liquid-crystalline medium comprising at least two liquid-crystalline components, wherein at least one component is an oxabicyclooctane compound of claim 10.

18. An electro-optical display element containing a liquid crystalline medium as claimed in claim 16.

19. An electro-optical display element containing a liquid-crystalline medium as claimed in claim 17.

* * * * *

UNITED STATES PATENT AND TRADEMARK OFFICE
CERTIFICATE OF CORRECTION

PATENT NO. : 6,808,762 B2
DATED : October 1, 2002
INVENTOR(S) : Matthias Bremer et al.

It is certified that error appears in the above-identified patent and that said Letters Patent is hereby corrected as shown below:

Column 45,
Line 5, delete "$L_3$" and insert -- $L^3$ --.

Signed and Sealed this

First Day of March, 2005

JON W. DUDAS
*Director of the United States Patent and Trademark Office*